(12) United States Patent
Bruggemann et al.

(10) Patent No.: US 9,475,859 B2
(45) Date of Patent: Oct. 25, 2016

(54) POLYNUCLEOTIDES ENCODING RODENT ANTIBODIES WITH HUMAN IDIOTYPES AND ANIMALS COMPRISING SAME

(71) Applicant: OMT, Inc., Palo Alto, CA (US)

(72) Inventors: Marianne Bruggemann, Cambridge (GB); Roland Buelow, Palo Alto, CA (US); Michael J. Osborn, Suffolk (GB); Biao Ma, Cambridge (GB)

(73) Assignee: OMT, Inc., San Diego, CA (US)

( * ) Notice: Subject to any disclaimer, the term of this patent is extended or adjusted under 35 U.S.C. 154(b) by 123 days.

(21) Appl. No.: 14/517,755

(22) Filed: Oct. 17, 2014

(65) Prior Publication Data

US 2015/0113668 A1    Apr. 23, 2015

Related U.S. Application Data

(63) Continuation of application No. PCT/US2013/075157, filed on Dec. 13, 2013.

(60) Provisional application No. 61/737,371, filed on Dec. 14, 2012.

(51) Int. Cl.
*A01K 67/027* (2006.01)
*C07K 16/00* (2006.01)

(52) U.S. Cl.
CPC ........... *C07K 16/00* (2013.01); *A01K 67/0275* (2013.01); *A01K 67/0278* (2013.01); *A01K 2227/105* (2013.01); *A01K 2267/01* (2013.01); *C07K 2317/24* (2013.01); *C07K 2317/52* (2013.01); *C07K 2317/56* (2013.01); *C07K 2317/64* (2013.01); *C07K 2317/92* (2013.01)

(58) Field of Classification Search
CPC ............... A01K 2227/105; A01K 2267/01; A01K 67/0275; A01K 67/0278; C07K 16/00; C07K 2317/24; C07K 2317/52; C07K 2317/56; C07K 2317/64; C07K 2317/92
USPC ............................................. 800/14, 18, 4, 6
See application file for complete search history.

(56) References Cited

U.S. PATENT DOCUMENTS 7,501,552 B2 † 3/2009 Lonberg

FOREIGN PATENT DOCUMENTS

| WO | WO 2008/151081    | † | 12/2008 |
| WO | WO2008/151081 A1 | * | 12/2008 |
| WO | WO 2011/004192    | † | 1/2011  |
| WO | WO 2011/158009 A1 |   | 12/2011 |

OTHER PUBLICATIONS

Cronkhite et al., "Male and female germline specific expression of an EGFP reporter gene in a unique strain of transgenic rats." Dev. Biol. vol. 284(1), pp. 171-183 (2005).
Davis et al., "Transgenic mice as a source of fully human antibodies for the treatment of cancer." Cancer Metastasis Rev, vol. 18, p. 421-425 (1999).
Hochi et al., "Successful production of transgenic rats." Animal Biotech vol. 1, pp. 175-184 (1990).
IgG heavy chain 2a gene segment (Rat Genome Database ID: 1359626) (4 pages) 2005.
IgM heavy chain constant gene segment (Rat Genome Database ID: 1359202) (4 pages) 2005.
Lonberg et al., "Antigen-specific human antibodies from mice comprising four distinct genetic modifications." Nature, vol. 368, pp. 856-859 (1994).
Ma et al., "Human antibody expression in transgenic rats: comparison of chimeric IgH loci with human VH, D and Jhbut bearing different rat C-gene regions." J. Immunol. Meth., vol. 400, pp. 78-86 (2013).
Mundt et al., "Novel control motif cluster in the IgH delta-gamma 3 interval exhibits B cell-specific enhancer function in early development." J. Immunol., vol. 166, pp. 3315 (2001).
Nicholson et al., "Antibody repertoires of four- and five-feature translocus mice carrying human immunoglobulin heavy chain and kappa and lambda light chain yeast artificial chromosomes." J. Immunol., vol. 163, p. 6898 (1999).
Osborn et al., "High-affinity IgG antibodies develop naturally in Ig-knockout rats carrying germline human IgH/Ig/Ig loci bearing the rat CH region." J. Immunology, vol. 190, No. 4, pp. 1481-1490 (2013).
Pettersson et al., "A second B cell-specific enhancer 3' of the immunoglobulin heavy-chain locus." Nature, vol. 344, pp. 165 168 (1990).
Pruzina et al., "Human monoclonal antibodies to HIV-1 gp140 from mice bearing YAC-based human immunoglobulin transloci." Protein Engineering, Design and Selection, vol. 1, pp. 791-799 (2011).
Vincent-Fabert et al., "Genomic deletion of the whole IgH 3' regulatory region (hs3a, hs1,2, hs3b, and hs4) dramatically affects class switch recombination and Ig secretion to all isotypes." Blood, vol. 116, pp. 1895-1898 (2010).

\* cited by examiner
† cited by third party

*Primary Examiner* — Janet Epps-Smith
(74) *Attorney, Agent, or Firm* — Todd A. Lorenz; Arnold & Porter LLP

(57) ABSTRACT

The invention relates to polynucleotides, particularly chimeric polynucleotides useful for optimal production of functional immunoglobulins with human idiotypes in rodents. The invention further relates to rodents comprising such polynucleotides.

17 Claims, 7 Drawing Sheets

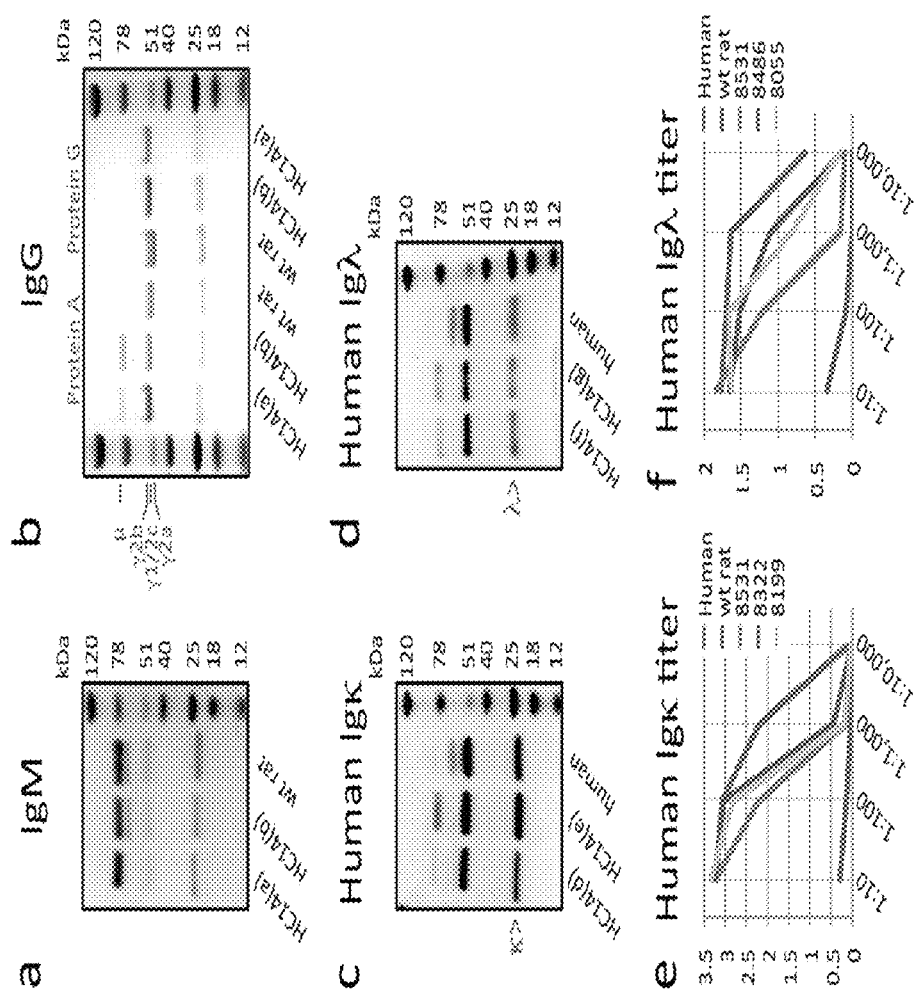

POLYNUCLEOTIDES ENCODING RODENT ANTIBODIES WITH HUMAN IDIOTYPES AND ANIMALS COMPRISING SAME

CROSS-REFERENCE TO RELATED APPLICATION

This application is a continuation of International Application No. PCT/US2013/075157 filed Dec. 13, 2013, which claims priority to U.S. provisional patent U.S. application Ser. No. 61/737,371 filed 14 Dec. 2012. The applications are expressly incorporated herein in their entirety by reference.

FIELD OF INVENTION

The invention relates to polynucleotides, particularly chimeric polynucleotides useful for the production of immunoglobulins with human idiotypes in rodents. The invention further relates to rodent cells comprising such polynucleotides.

REFERENCE TO A SEQUENCE LISTING

A Sequence Listing is provided in this patent document as a txt file entitled "189314-US_ST25.txt" and created Dec. 12, 2012 (size 3 MB). The contents of this file is incorporated herein by reference in its entirety.

BACKGROUND OF THE INVENTION

Human monoclonal antibodies have proven to be invaluable in therapeutic applications, either as IgG of conventional size, single chains or domain modules[1, 2]. Despite the successes there are still major shortcomings in their production, which relies either on specificity selection of available human material and subsequent modification of individual products, or the immunization of the limited availability of transgenic animals, mainly mice[3]. Target antigen restrictions are widely in place for the use of transgenic mice, as well as large transgenic animals such as cattle, and the development of new specificities is company controlled[4-7].

DNA rearrangement and expression of human immunoglobulin (Ig) genes in transgenic mice was pioneered over 20 years ago by stably inserting heavy-chain genes in germline configuration[8]. Although human antibody repertoires were obtained in these early animals, major improvements, resulting in higher expression levels and exclusive production of human Ig, combined two new strategies: gene knock-out in embryonic stem (ES) cells[9] and locus extension on artificial chromosomes[10].

Silencing of the endogenous Ig genes by gene targeting in ES cells produced several inactive mouse lines without the ability to rearrange their IgH and IgK locus or without producing fully functional IgH, IgK or IgX products (summarized in[3]). More recently zinc finger nucleases (ZFNs) were designed to generate site-specific double-strand breaks in Ig genes, which allowed gene disruption by deletion and non-homologous DNA repair. Injection of ZFN plasmids into fertilized eggs produced Ig silenced rats and rabbits with IgH and IgL disruptions[11-13].

Efficient expression of antibodies requires functional regulatory elements in various locations in immunoglobulin loci. Enhancer sequences have been identified near many active genes by nuclease digest and hypersensitivity to degradation. Hypersensitive sites may precede promoter sequences and the strength of their activity was correlated with the DNA sequence. Linkage to reporter genes showed elevated transcription if enhancer function was present (Mundt et al., J. Immunol., 166, 3315[2001]. In the IgH locus two important transcription or expression regulators have been identified, Eμ and the 3'E at the end of the locus (Pettersson et al., Nature, 344, 165 [1990]). In the mouse the removal of the entire 3' regulatory region (containing hs3a, hs1,2, hs3b and hs4) allows normal early B-cell development but abrogates class-switch recombination (Vincent-Fabert et al., Blood, 116, 1895 [2010]) and possibly prevents the optimization of somatic hypermutation (Pruzina et al., Protein Engineering, Design and Selection, 1, [2011]).

The regulatory function to achieve optimal isotype expression is particularly desirable when transgenic human IgH genes are being used. However, in a number of laboratories, transgene constructs with an incomplete 3'E region, typically providing only the hs1,2 element, led to disappointing expression levels in transgenic mice even when the endogenous IgH locus was knocked-out. This may be one reason why the generation of antigen-specific fully human IgGs from genetically engineered mice has been inefficient thus far. (Lonberg et al., Nature 368, 856 [1994]; Nicholson et al., J. Immunol., 163, 6898 [1999]; Davis et al., Cancer Metastasis Rev. 18, 421 [1999]; Pruzina et al., Protein Engineering, Design and Selection, 1, [2011].

In the rat, the 3'E region has only been poorly analyzed. A comparison of mouse and rat sequences does not allow identification of hs4, the crucial 4th E element with additional important regulatory sequences further downstream (Chatterjee et al., J. Biol. Chem., 286, 29303 [2011]). This could mean the region is not present in the rat, and perhaps not as important as in the mouse, or it could be absent in the analyzed rat genome sequences.

Still needed are methods and materials for the optimal production of immunoglobulins or antibodies having human idiotypes using transgenic animals, which are useful for treating humans in a broad range of disease areas.

SUMMARY OF INVENTION

Disclosed herein are novel polynucleotides comprising nucleic acid sequences encoding chimeric immunoglobulin chains, particularly chimeric heavy chains for use in creating transgenic animals. The polynucleotides of the present invention advantageously provide optimal expression due, at least in part, to the inclusion of a 3' enhancer since transloci lacking this 3' enhancer result in impaired isotype switching and low IgG expression. Accordingly, in preferred embodiments the invention provides chimeric polynucleotides comprising a rat 3' enhancer sequence, an Ig constant region gene and at least one human immunoglubulin (Ig) joining (J) region gene. In a preferred embodiment, the rat 3' enhancer sequence comprises the sequence set forth as SEQ ID NO:1, or a portion thereof.

The chimeric polynucleotides set forth herein may further comprise at least one human variable (V) gene, at least one a diversity (D) gene, or a combination thereof. In one embodiment, the constant region gene of the chimeric polynucleotide is selected from the group consisting of a human constant region gene and a rat constant region gene. In a preferred embodiment, the constant region gene is a rat constant region gene. In another preferred embodiment, the constant region gene is selected from the group consisting of Cμ and Cγ.

In one embodiment, the chimeric polynucleotide comprises a nucleic acid sequence substantially homologous to the bacterial artificial chromosome (BAC) Annabel disclosed herein (e.g., SEQ ID NO:10), or a portion thereof, and may optionally further comprise at least one human variable Ig gene isolatable from BAC6-$V_H$3-11 and BAC3. In a preferred embodiment, the chimeric polynucleotides contemplated herein comprise nucleic acid sequences (a) and (b) in 5' to 3' order: (a) a human Ig variable region comprising human V genes in natural configuration isolatable from BAC6-$V_H$3-11 and/or BAC3, and (b) a human Ig joining region comprising human J genes in natural configuration isolatable from the BAC Annabel. In another embodiment, each of the human Ig variable region, human Ig diversity region, human Ig joining region, the Ig constant region and the rat 3' enhancer region of a chimeric polynucleotide as disclosed herein are in the relative positions as shown in FIG. 1a. In another embodiment, a chimeric polynucleotide as disclosed has a sequence comprising or substantially homologous to the sequence set forth as SEQ ID NO:2 or a portion thereof. In another embodiment, a chimeric polynucleotide as disclosed has a sequence comprising or substantially homologous to the sequence set forth as SEQ ID NO:11, or a portion thereof. In a further embodiment, a chimeric polynucleotoide as disclosed herein comprises a rearranged V-D-J regions, wherein said rearranged V-D-J regions encode a heavy chain variable domain exon.

Also disclosed herein are polynucleotides encoding human kappa light chain genes. In one embodiment, a polynucleotide as disclosed herein has a nucleic acid sequence comprising or substantially homologous to a nucleic acid sequence selected from the group consisting of RP11-1156D9 (set forth as SEQ ID NO:3) and RP11-1134E24 (set forth as SEQ ID NO:4). In another embodiment, the isolated polynucleotide comprises nucleic acid sequences (a) and (b) in 5' to 3' order: (a) a human Ig variable region comprising human V genes in natural configuration isolatable from bacterial artificial chromosomes (BAC) RP11-156D9 and/or RP11-1134E24; (b) a human Ig joining region comprising human J genes in natural configuration isolatable from the bacterial artificial chromosomes (BAC) RP11-1134E24 and/or RP11-344F17 (set forth as SEQ ID NO:5). In a preferred embodiment, each of the human Ig variable region, the human Ig joining region, and the human Ig constant region are in relative position as shown in FIG. 1b. In another embodiment, a chimeric polynucleotide as disclosed has a sequence comprising or substantially homologous to the sequence set forth as SEQ ID NO:6 or a portion thereof.

Also provided herein is a rodent cell comprising one or more polynucleotides of the invention. For example, provided herein is a rodent cell comprising a polynucleotide as disclosed herein, preferably comprising a nucleic acid sequence encoding for a chimeric heavy chain, e.g., a nucleic acid sequence encoding a rat 3' enhancer sequence, an Ig constant region gene and at least one human J region gene, and optionally, comprising a nucleic acid sequence substantially homologous to the nucleic acid sequence selected from the group consisting of RP11-1156D9, RP11-1134E24 and portions thereof. The rodent cell contemplated herein may further comprise a polynucleotide encoding a functional light chain, e.g., having a nucleic acid sequence comprising or substantially homologous to a nucleic acid sequence selected from the group consisting of the sequence shown in FIG. 1b (set forth as SEQ ID NO:6), the sequence shown in FIG. 1c (set forth as SEQ ID NO:7), and portions thereof. In one embodiment, one or more of the polynucleotides are integrated into the rodent cell genome.

BRIEF DESCRIPTION OF THE DRAWINGS

In FIG. 2a, A refers to pro/pre B-cells (CD45R$^+$IgM$^-$) and B refers to immature B-cells (CD45R$^+$IgM$^+$). In FIG. 2c, A refers to transitional B cells (CD45R$^+$IgM$^-$), B to follicular B cells (CD45R$^+$IgM$^+$) and C to marginal zone B cells (CD45R$^{low}$IgM$^+$).

FIG. 4: Purification of rat Ig with human idiotypes and comparison to human and normal rat Ig levels. OmniRat serum and human or rat wt control serum, 100 µl each, was used for IgM/G purification. (a) IgM was captured with anti-IgM matrix, which identified 14 µg in wt rat, and 30 µg and 10 µg in OmniRats [HC14(a) and HC14(c)]. (b) IgG was purified on protein A and protein G columns, with a yield of up to ~3 mg/ml for OmniRats (Protein A: HC14(a) 1000 µg/ml; HC14(b) 350 µg/ml; wt rat 350 µg/ml; Protein G: HC14(a) 2970 µg/ml; HC14(b) 280 µg/ml; wt rat 1010 µg/ml). (c) Human IgK and (d) human IgX was purified on anti-IgK and anti-IgX matrix, respectively. No purification product was obtained using wt rat serum (not shown). Purified Ig, ~3 µg (concentration determined by nano drop), was separated on 4-15% SDS-PAGE under reducing conditions. Comparison by ELISA titration of (e) human IgK and (f) human IgX levels in individual OmniRats (8531, 8322, 8199, 8486, 8055), human and wt rat serum. Serum dilution (1:10, 1:100, 1:1,000, 1:10,000) was plotted against binding measured by adsorption at 492 nm. Matching name/numbers refer to samples from the same rat.

DETAILED DESCRIPTION

Figure 1:
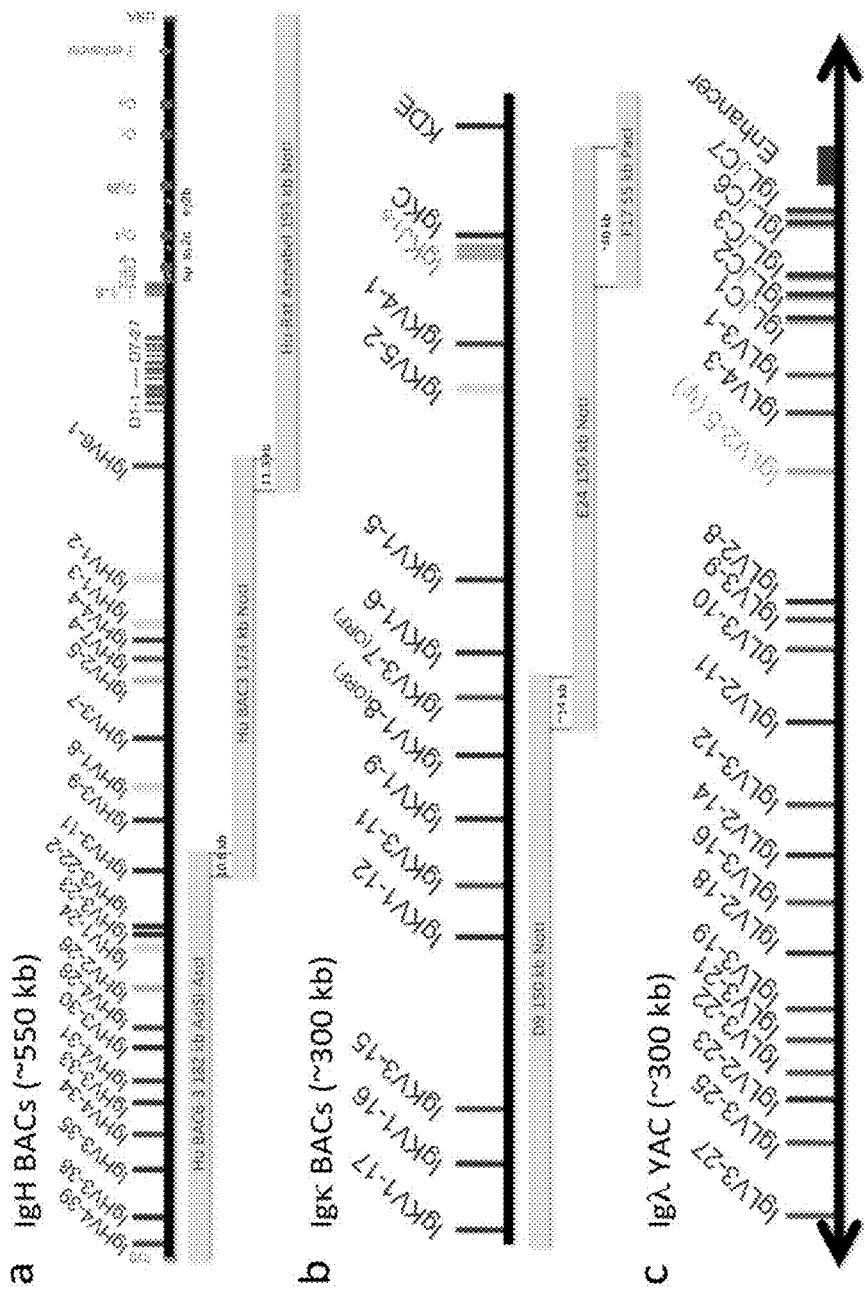
FIG. 1: Integrated human Ig loci. (a) The chimeric human-rat IgH region contains 3 overlapping BACs with 22 different and potentially functional human $V_H$ segments. BAC6-3 has been extended with $V_H$3-11 to provide a 10.6 kb overlap to BAC3, which overlaps 11.3 kb via $V_H$6-1 with the C region BAC Hu-Rat Annabel. The latter is chimeric and contains all human D and $J_H$ segments followed by the rat C region with full enhancer sequences. (b) The human Igκ BACs with 12 Vκs and all Jκs provide a ~14 kb overlap in the Vκ region and ~40 kb in Cκ to include the KDE. (c) The human Igl region with 17 Vls and all J-Cls, including the 3' enhancer, is from a YAC[33].
Figure 2A:
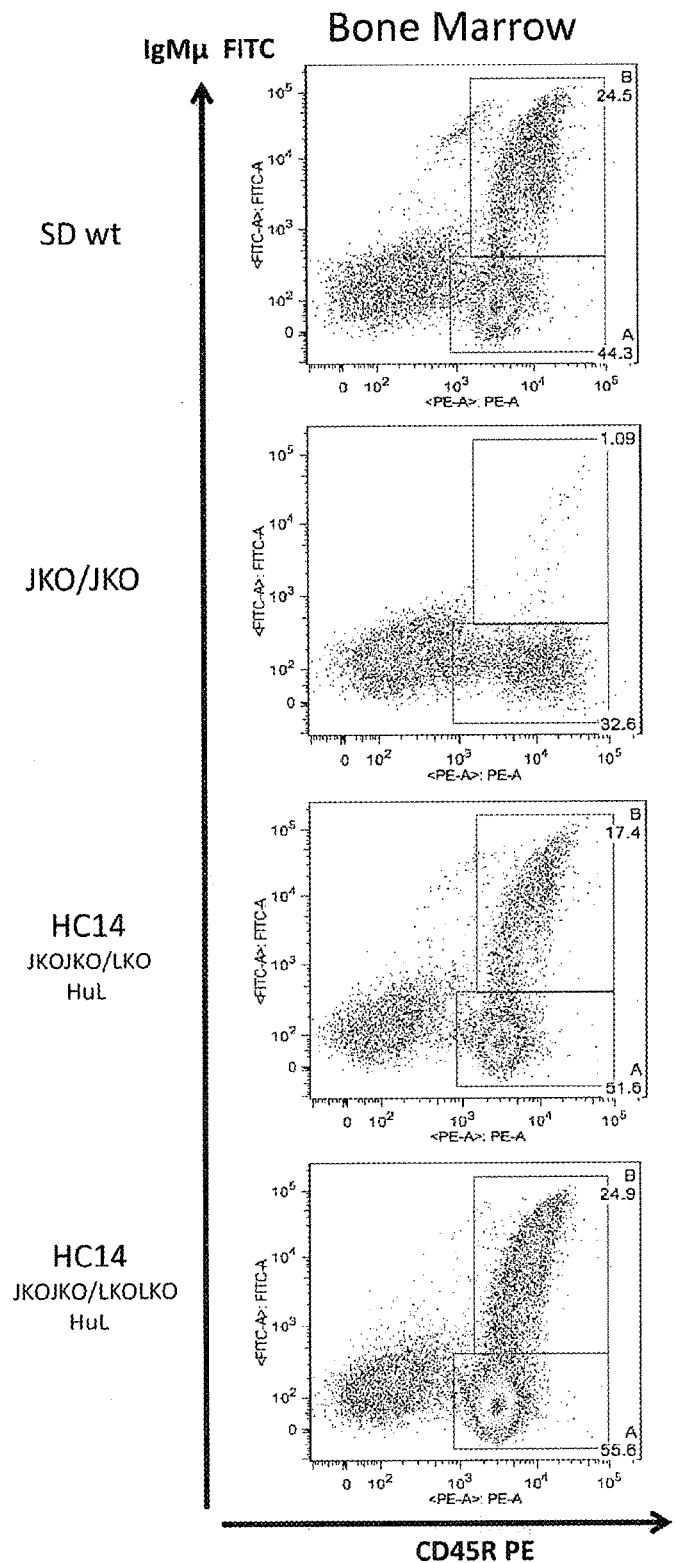
FIG. 2a-d: Flow cytometry analysis of lymphocyte-gated bone marrow and spleen cells from 3 months old rats. Surface staining for IgM and CD45R (B220) revealed a similar number of immature and mature B-cells in bone marrow and spleen of HC14 and wt rats, while JKO/JKO animals showed no B-cell development. Plotting forward (FSC) against site (SSC) scatter showed comparable numbers of lymphocyte (gated) populations, concerning size and shape. Surface staining of spleen cells with anti-IgG (G1, G2a, G2b, G2c isotype) plotted against cell count (×102) revealed near normal numbers of IgG+ expressers in HC14 rats compared to wt.
Figure 2B:
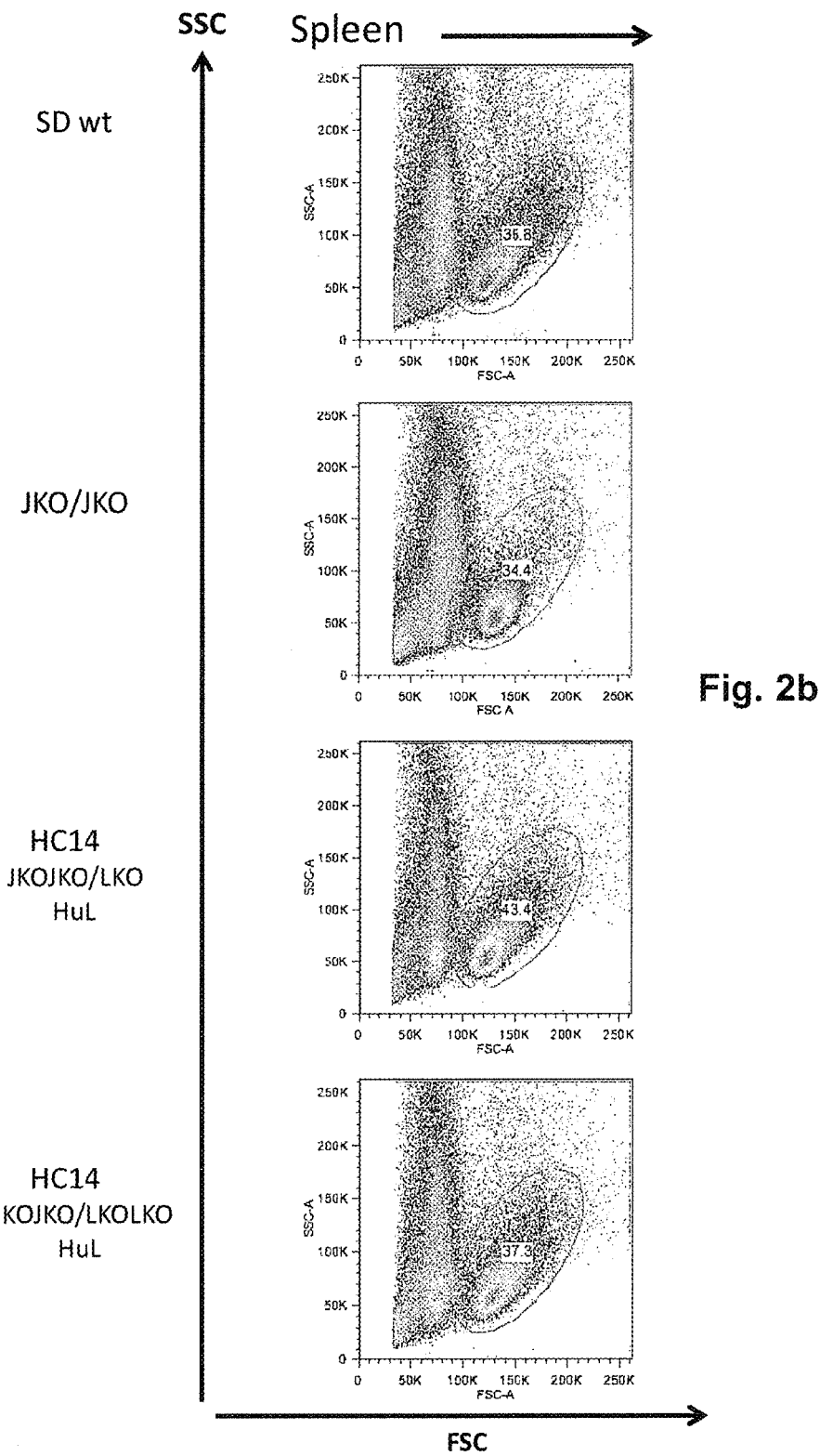
Figure 2C:
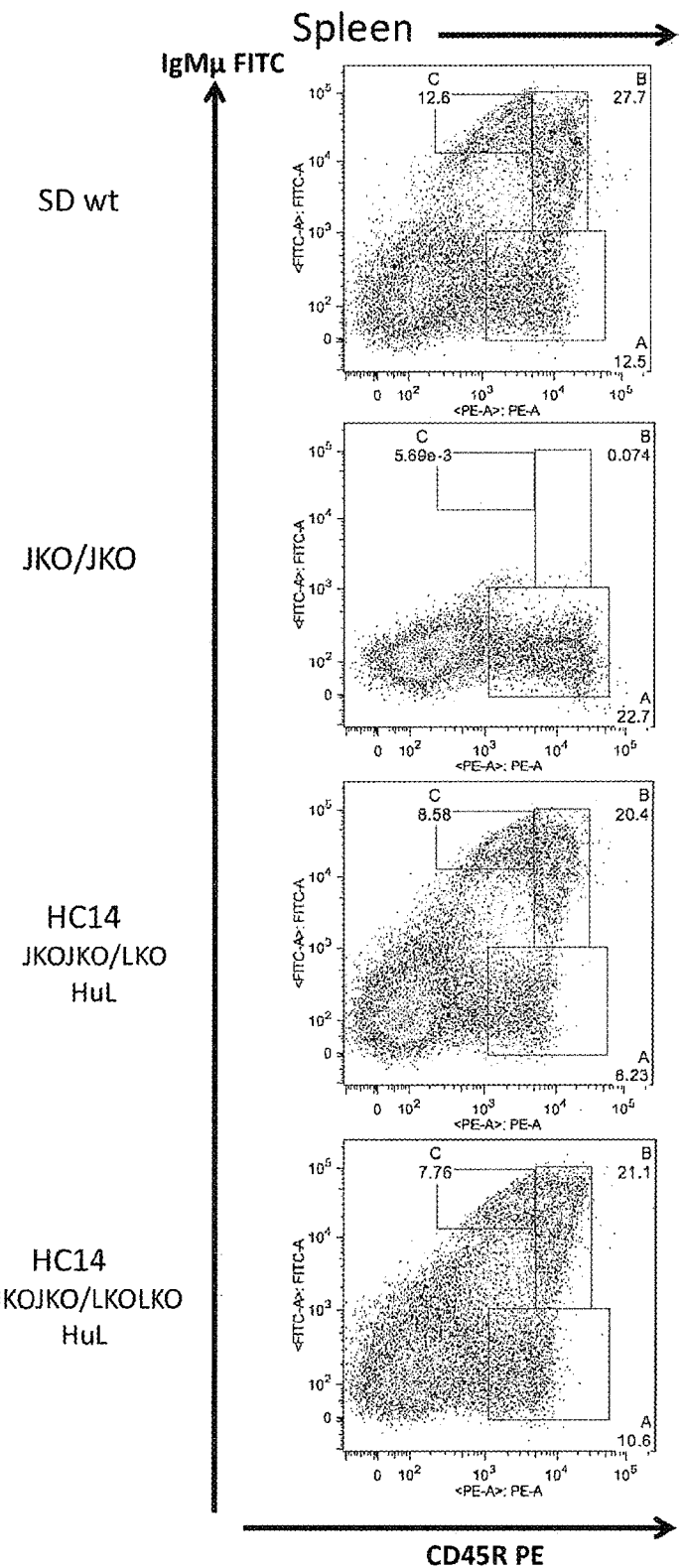
Figure 2D:
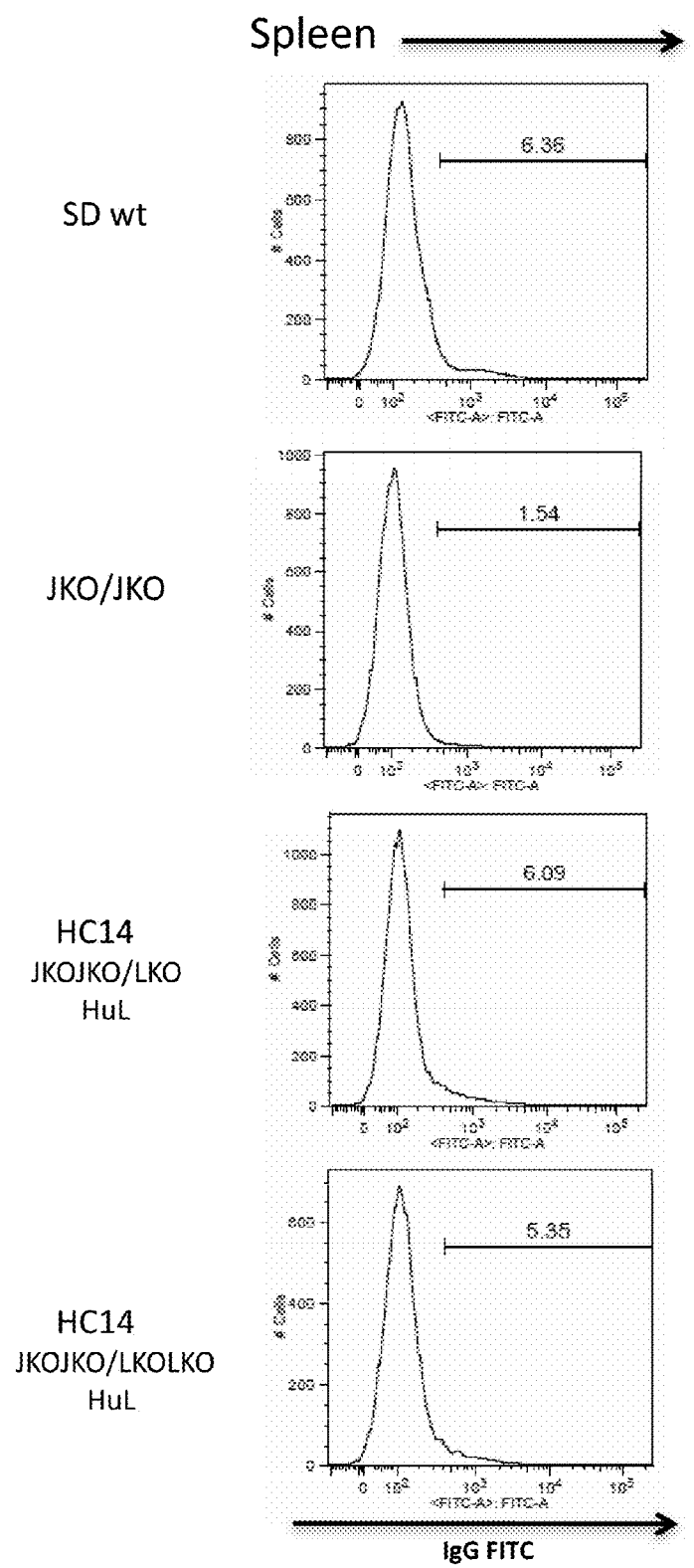

Provided herein are chimeric polynucleotides encoding a recombinant or artificial immunoglobulin chain or loci. As described above, the chimeric polynucleotides disclosed herein are useful for the transformation of rodents to include human Ig genes and for the production of immunoglobulins or antibodies having human idiotypes using such rodents.

Polynucleotides

Immunoglobulin refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd, or 214 amino acids) generally comprise a variable domain encoded by an exon comprising one or more variable region gene(s) and one or more joining region gene(s) at the $NH_2$-terminus (about 110 amino acids) and constant domain encoded by a kappa or lambda constant region gene at the COOH-terminus. Full-length immunoglobulin "heavy chains" (about 50 Kd, or 446 amino acids), similarly comprise (1) a variable domain (about 116 amino acids) encoded by an exon comprising one or more variable region genes, one or more diversity region genes and one or more joining region genes, and (2) one of the aforementioned constant domains comprising one or more constant region genes, e.g., alpha, gamma, delta, epsilon or mu (encoding about 330 amino acids). The immunoglobulin heavy chain constant region genes encode for the antibody class, i.e., isotype (e.g., IgM or IgG1).

As used herein, the term "antibody" refers to a protein comprising at least one, and preferably two, heavy (H) chain variable domains (abbreviated herein as VH), and at least one and preferably two light (L) chain variable domains (abbreviated herein as VL). An ordinarily skilled artisan will recognize that the variable domain of an immunological chain is encoded in gene segments that must first undergo somatic recombination to form a complete exon encoding the variable domain. There are three types of regions or gene segments that undergo rearrangement to form the variable domain: the variable region comprising variable genes, the diversity region comprising diversity genes (in the case of an immunoglobulin heavy chain), and the joining region comprising joining genes. The VH and VL domains can be further subdivided into regions of hypervariability, termed "complementarity determining regions" ("CDRs") interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242; and Chothia et al. (1987) J. Mol. Biol. 196:901-17, which are hereby incorporated by reference). Each VH and VL domain is generally composed of three CDRs and four FRs, arranged from amino-terminus to carboxy-terminus in the following order: FR1, CDR1, FR2, CDR2, FR3, CDR3, FR4. The antigen binding fragment of an antibody (or simply "antibody portion," or "fragment"), as used herein, refers to one or more fragments of a full-length antibody that retain the ability to specifically bind to an antigen (e.g., CD3).

Examples of binding fragments encompassed within the term "antigen binding fragment" of an antibody include (i) an Fab fragment, a monovalent fragment consisting of the VL, VH, CL and CH1 domains; (ii) an $F(ab)_2$ fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al. (1989) Nature 341:544-46), which consists of a VH domain; and (vi) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-26; and Huston et al. (1988) Proc. Natl. Acad. Sci. USA 85:5879-83). Such single chain antibodies are also intended to be encompassed within the term "antigen binding fragment" of an antibody. These antibody fragments are obtained using conventional techniques known to those skilled in the art, and the fragments are screened for utility in the same manner as are intact antibodies.

An antibody may further include a heavy and/or light chain constant domain to thereby form a heavy and light immunoglobulin chain, respectively. In one embodiment, the antibody is a tetramer of two heavy immunoglobulin chains and two light immunoglobulin chains, wherein the heavy and light immunoglobulin chains are interconnected, e.g., by disulfide bonds. The heavy chain constant domain is comprised of three gene segments, CH1, CH2 and CH3. The light chain constant domain is comprised of one gene, CL. The variable domains of the heavy and/or light chains contain a binding domain that interacts with an antigen. The constant domains of the antibodies typically mediate the binding of the antibody to host tissues or factors, including various cells of the immune system (e.g., effector cells) and the first component (C1q) of the classical complement system.

By polynucleotide encoding an artificial immunoglobulin locus or artificial immunoglobulin chain is meant an recombinant polynucleotide comprising multiple immunoglobulin regions, e.g., a variable (V) region or gene segment comprising V genes, a joining (J) gene region or gene segment comprising J genes, a diversity (D) region or gene segment comprising D genes in the case of a heavy chain locus and/or at least one constant (C) region comprising at least one C gene. Preferably, each region of the variable domain, e.g., V, D, or J region, comprises or spans at least two genes of the same type. For example a variable region as used herein comprises at least two variable genes, a joining region comprises at least two joining genes and a diversity region comprises two diversity genes. A constant region may comprise only one constant gene, e.g. a κ gene or λ gene, or multiple genes, e.g., CH1, CH2, and CH3.

"Enhancer sequences" or "enhancer" as used herein refers to sequences that have been identified near many active genes by nuclease digest and hypersensitivity to degradation. Hypersensitive sites may precede promoter sequences and the strength of their activity was correlated with the DNA sequence. Linkage to reporter genes showed elevated transcription if enhancer function was present (Mundt et al., J. Immunol., 166, 3315[2001]). In the IgH locus two important transcription or expression regulators have been identified, Eμ and the 3'E at the end of the locus (Pettersson et al., Nature, 344, 165 [1990]). In the mouse the removal of the whole 3' regulatory region (containing hs3a, hs1,2, hs3b and hs4) allows normal early B-cell development but abrogates class-switch recombination (Vincent-Fabert et al., Blood, 116, 1895 [2010]) and possibly prevents the optimization of somatic hypermutation (Pruzina et al., Protein Engineering, Design and Selection, 1, [2011]). The regulatory function to achieve optimal isotype expression is particularly desirable when transgenic human IgH genes are being used. Transgene constructs with incomplete 3'E region, usually only providing the hs1,2 element, led to disappointing expression levels in transgenic mice even when the endogenous IgH locus was knocked-out. As a consequence, only few antigen-specific fully human IgGs have been isolated from constructs produced in the last 20 years (Lonberg et al., Nature 368, 856 [1994]; Nicholson et al., J. Immunol., 163, 6898 [1999]; Davis et al., Cancer Metastasis Rev. 18, 421 [1999]; Pruzina et al., Protein Engineering, Design and Selection, 1, [2011]). In the rat IgH locus, the 3'E region has only been poorly analyzed. A comparison of mouse and rat sequences did not allow identification of hs4, the crucial 4th element with additional important regulatory sequences further downstream (Chatterjee et al., J. Biol. Chem., 286, 29303 [2011]). The polynucleotides of the present invention advantageously provide optimal expression due, at least in part, to the inclusion of a rat 3' enhancer since chimeric polynucleotides lacking this 3' enhancer result in impaired isotype switching and low IgG expression. In one embodiment, the rat 3' enhancer has a sequence comprising or substantially homologous to the sequence set forth as SEQ ID NO:1 or a portion thereof.

As used herein, a polynucleotide having a sequence comprising or substantially homologous to a portion, e.g., less than the entirety, of second sequence (e.g., SEQ ID NO:1, SEQ ID NO:2, etc.) preferably retains the biological activity of the second sequence (e.g., retains the biological activity of a 3' enhancer to provide optimal expression and/or isotype switching of immunoglobulins, is capable of rearrangement to provide a humanized chimeric heavy chain, etc.). In one embodiment, a nucleic acid comprising a sequence comprising or substantially homologous to a portion of SEQ ID NO:1 comprise at least 8 kB, preferably at least 10 kB of continuous nucleic acids that are substantially homologous to SEQ ID NO:1.

"Artificial Ig locus" as used herein may refer to polynucleotides that (e.g., a sequence comprising V-, D-, and/or J regions in the case of heavy chain, or V- and/or J regions in the case of light chain, and optionally a constant region for either or both a heavy and light chgin) that are unrearranged, partially rearranged, or rearranged. Artificial Ig loci include artificial Ig light chain loci and artificial Ig heavy chain loci. In one embodiment, an artificial immunoglobulin locus of the invention is functional and capable of rearrangement and producing a repertoire of immunoglobulin chains. In a preferred embodiment, the variable domain or portion thereof of a polynucleotide disclosed herein comprises genes in natural configuration, i.e., naturally occurring sequences of an human Ig gene segment, degenerate forms of naturally occurring sequences of a human Ig gene segment, as well as synthetic sequences that encode a polypeptide sequence substantially identical to the polypeptide encoded by a naturally occurring sequence of a human Ig gene segment. In another preferred embodiment, the polynucleotide comprises a variable domain or portion thereof in a natural configuration found in humans. For example, a polynucleotide encoding an artificial Ig heavy chain as disclosed herein may comprise in natural configuration at least two human V genes, at least two D genes, at least two J genes or a combination thereof.

In a preferred embodiment, an artificial Ig locus comprises a non-human C region gene and is capable of producing a repertoire of immunoglobulins including chimeric immunoglobulins having a non-human C region. In one embodiment, an artificial Ig locus comprises a human C region gene and is capable of producing a repertoire of immunoglobulins including immunoglobulins having a human C region. In one embodiment, an artificial Ig locus comprises an "artificial constant region gene", by which is meant a constant region gene comprising nucleotide sequences derived from human and non-human constant regions genes. For example, an exemplary artificial C constant region gene is a constant region gene encoding a human IgG CH1 domain and rat IgG CH2 and CH3 domain.

In a preferred embodiment, an artificial Ig locus comprises 3' enhancer sequences, including hs1,2, hs3a, hs3b and sequences (500-2500 nt) downstream of hs3b. In transgenic animals, artificial loci comprising the full ~30 kb 3'E region from Calpha to 3' hs3b result in high level IgG expression, extensive hypermutation and large numbers of antigen-specific hybridomas of high (pM) affinity. However, shorter enhancer sequences reduce Ig expression.

In a preferred embodiment, an artificial Ig locus comprises the 3' enhancer sequence shown in FIG. 1a. This sequence is derived from the rat Ig heavy chain locus and contains about 30 kb of the 3' region from Calapha to 3' hs3b. The sequence of the rat 3' enhancer sequence is set forth as SEQ ID NO:1. In another embodiment, the artificial Ig locus comprises a sequence comprising or substantially homologous to the sequence set forth as SEQ ID NO:1, or a portion thereof.

In some embodiments, an artificial Ig heavy chain locus lacks CH1, or an equivalent sequence that allows the resultant immunoglobulin to circumvent the typical immunoglobulin: chaperone association. Such artificial loci provide for the production of heavy chain-only antibodies in transgenic animals which lack a functional Ig light chain locus and hence do not express functional Ig light chain. Such artificial Ig heavy chain loci are used in methods contemplated herein to produce transgenic animals lacking a functional Ig light chain locus, and comprising an artificial Ig heavy chain locus, which animals are capable of producing heavy chain-only antibodies. Alternatively, an artificial Ig locus may be manipulated in situ to disrupt CH1 or an equivalent region and generate an artificial Ig heavy chain locus that provides for the production of heavy chain-only antibodies. Regarding the production of heavy chain-only antibodies in light chain-deficient mice, see for example Zou et al., JEM, 204:3271-3283, 2007.

By "human idiotype" is meant a polypeptide sequence present on a human antibody encoded by an immunoglobulin V-gene segment. The term "human idiotype" as used herein includes both naturally occurring sequences of a human antibody, as well as synthetic sequences substantially identical to the polypeptide found in naturally occurring human antibodies. By "substantially" is meant that the degree of amino acid sequence identity is at least about 85%-95%. Preferably, the degree of amino acid sequence identity is greater than 90%, more preferably greater than 95%.

By a "chimeric antibody" or a "chimeric immunoglobulin" is meant an immunoglobulin molecule comprising a portion of a human immunoglobulin polypeptide sequence (or a polypeptide sequence encoded by a human Ig gene segment) and a portion of a non-human immunoglobulin polypeptide sequence. The chimeric immunoglobulin molecules of the present invention are immunoglobulins with non-human Fc-regions or artificial Fc-regions, and human idiotypes. Such immunoglobulins can be isolated from animals of the invention that have been engineered to produce chimeric immunoglobulin molecules.

By "artificial Fc-region" is meant an Fc-region encoded by an artificial constant region gene.

The term "Ig gene segment" as used herein refers to regions of DNA encoding various portions of an Ig molecule, which are present in the germline of non-human animals and humans, and which are brought together in B cells to form rearranged Ig genes. Thus, Ig gene segments as used herein include V gene segments, D gene segments, J gene segments and C gene segments.

The term "human Ig gene segment" as used herein includes both naturally occurring sequences of a human Ig gene segment, degenerate forms of naturally occurring sequences of a human Ig gene segment, as well as synthetic sequences that encode a polypeptide sequence substantially identical to the polypeptide encoded by a naturally occurring sequence of a human Ig gene segment. By "substantially" is meant that the degree of amino acid sequence identity is at least about 85%-95%. Preferably, the degree of amino acid sequence identity is greater than 90%, more preferably greater than 95%

Polynucleotides related to the present invention may comprise DNA or RNA and may be wholly or partially synthetic. Reference to a nucleotide sequence as set out herein encompasses a DNA molecule with the specified sequence, and encompasses an RNA molecule with the specified sequence in which U is substituted for T, unless context requires otherwise.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent sequence identity between two sequences may be accomplished using a mathematical algorithm. In a preferred embodiment, the percent identity between two amino acid sequences is determined using the Needleman and Wunsch ((1970) J. Mol. Biol. 48:444-53) algorithm, which has been incorporated into the GAP program in the GCG software package (available online at gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is a Blossum 62 scoring matrix with a gap penalty of 12, a gap extend penalty of 4, and a frameshift gap penalty of 5. The percent identity between two amino acid or nucleotide sequences can also be determined using the algorithm of Meyers and Miller ((1989) CABIOS 4:11-17), which has been incorporated into the ALIGN program (version 2.0), using a PAM120 weight residue table, a gap length penalty of 12 and a gap penalty of 4.

Artificial Ig Loci

The present invention is further directed to artificial Ig loci and their use in making transgenic animals capable of producing immunoglobulins having a human idiotype. Each artificial Ig locus comprises multiple immunoglobulin gene segments, which include at least one V region gene segment, one or more J gene segments, one or more D gene segments in the case of a heavy chain locus, and one or more constant region genes. In the present invention, at least one of the V gene segments encodes a germline or hypermutated human V-region amino acid sequence. Accordingly, such transgenic animals have the capacity to produce a diversified repertoire of immunoglobulin molecules, which include antibodies having a human idiotype. In heavy chain loci human or non-human-derived D-gene segments may be included in the artificial Ig loci. The gene segments in such loci are juxtaposed with respect to each other in an unrearranged configuration (or "the germline configuration"), or in a partially or fully rearranged configuration. The artificial Ig loci have the capacity to undergo gene rearrangement (if the gene segments are not fully rearranged) in the subject animal thereby producing a diversified repertoire of immunoglobulins having human idiotypes.

Regulatory elements like promoters, enhancers, switch regions, recombination signals, and the like may be of human or non-human origin. What is required is that the elements be operable in the animal species concerned, in order to render the artificial loci functional. Preferred regulatory elements are described in more detail herein.

In one aspect, the invention provides transgenic constructs containing an artificial heavy chain locus capable of undergoing gene rearrangement in the host animal thereby producing a diversified repertoire of heavy chains having human idiotypes. An artificial heavy chain locus of the transgene contains a V-region with at least one human V gene segment. Preferably, the V-region includes at least about 5-100 human heavy chain V (or "VH") gene segments. As described above, a human VH segment encompasses naturally occurring sequences of a human VH gene segment, degenerate forms of naturally occurring sequences of a human VH gene segment, as well as synthetic sequences that encode a polypeptide sequence substantially (i.e., at least about 85%-95%) identical to a human heavy chain V domain polypeptide.

In a preferred embodiment, the artificial heavy chain locus contains at least one or several rat constant region genes, e.g., Cδ, Cμ and Cγ (including any of the Cγ subclasses).

In another preferred embodiment, the artificial heavy chain locus contains artificial constant region genes. In a preferred embodiment, such artificial constant region genes encode a human CH1 domain and rat CH2 CH3 domains, or a human CH1 and rat CH2, CH3 and CH4 domains. A hybrid heavy chain with a human CH1 domain pairs effectively with a fully human light chain.

In a preferred embodiment, an artificial Ig locus comprises 3' enhancer sequences, including hs1,2, hs3a, hs3b and sequences between rat Calpha and 3'hs3b.

In another preferred embodiment, the artificial heavy chain locus contains artificial constant region genes lacking CH1 domains In a preferred embodiment, such artificial constant region genes encode truncated IgM and/or IgG lacking the CH1 domain but comprising CH2, and CH3, or CH1, CH2, CH3 and CH4 domains. Heavy chains lacking CH1 domains cannot pair effectively with Ig light chains and form heavy chain only antibodies.

In another aspect, the invention provides transgenic constructs containing an artificial light chain locus capable of undergoing gene rearrangement in the host animal thereby producing a diversified repertoire of light chains having human idiotypes. An artificial light chain locus of the transgene contains a V-region with at least one human V gene segment, e.g., a V-region having at least one human VL gene and/or at least one rearranged human VJ segment. Preferably, the V-region includes at least about 5-100 human light chain V (or "VL") gene segments. Consistently, a human VL segment encompasses naturally occurring sequences of a human VL gene segment, degenerate forms of naturally occurring sequences of a human VL gene segment, as well as synthetic sequences that encode a polypeptide sequence substantially (i.e., at least about 85%-95%) identical to a human light chain V domain polypeptide. In one embodiment, the artificial light chain Ig locus has a C-region having at least one rat C gene (e.g., rat Cλ or Cκ).

Another aspect of the present invention is directed to methods of making a transgenic vector containing an artificial Ig locus. Such methods involve isolating Ig loci or fragments thereof, and combining the same, with one or several DNA fragments comprising sequences encoding human V region elements. The Ig gene segment(s) are inserted into the artificial Ig locus or a portion thereof by ligation or homologous recombination in such a way as to retain the capacity of the locus to undergo effective gene rearrangement in the subject animal.

Preferably, a non-human Ig locus is isolated by screening a library of plasmids, cosmids, YACs or BACs, and the like, prepared from the genomic DNA of the same. YAC clones can carry DNA fragments of up to 2 megabases, thus an entire animal heavy chain locus or a large portion thereof can be isolated in one YAC clone, or reconstructed to be contained in one YAC clone. BAC clones are capable of carrying DNA fragments of smaller sizes (about 50-500 kb). However, multiple BAC clones containing overlapping fragments of an Ig locus can be separately altered and subsequently injected together into an animal recipient cell, wherein the overlapping fragments recombine in the recipient animal cell to generate a continuous Ig locus.

Human Ig gene segments can be integrated into the Ig locus on a vector (e.g., a BAC clone) by a variety of methods, including ligation of DNA fragments, or insertion of DNA fragments by homologous recombination. Integration of the human Ig gene segments is done in such a way that the human Ig gene segment is operably linked to the host animal sequence in the transgene to produce a functional humanized Ig locus, i.e., an Ig locus capable of gene rearrangement which lead to the production of a diversified repertoire of antibodies with human idiotypes. Homologous recombination can be performed in bacteria, yeast and other cells with a high frequency of homologous recombination events. Engineered YACs and BACs can be readily isolated from the cells and used in making transgenic animals Rodent Oocytes and Transgenic Animals Comprising Artificial Ig Loci and Capable of Producing Antibodies Having Human Idiotypes In one aspect, the invention provides transgenic animals capable of producing immunoglobulins having human idiotypes, as well as methods of making the same.

The transgenic animals used are selected from rodents (e.g., rats, hamsters, mice and guinea pigs).

The transgenic animals used for humanized antibody production in the invention carry germline mutations in endogenous Ig loci. In a preferred embodiment, the transgenic animals are homozygous for mutated endogenous Ig heavy chain and/or endogenous Ig light chain genes. Further, these animals carry at least one artificial Ig locus that is functional and capable of producing a repertoire of immunoglobulin molecules in the transgenic animal. The artificial Ig loci used in the invention include at least one human V gene segment.

In a preferred embodiment, the transgenic animals carry at least one artificial Ig heavy chain locus and at least one artificial Ig light chain locus that are each functional and capable of producing a repertoire of immunoglobulin molecules in the transgenic animal, which repertoire of immunoglobulin molecules includes antibodies having a human idiotype. In one embodiment, artificial loci including at least one non-human C gene are used, and animals capable of producing chimeric antibodies having a human idiotype and non-human constant region are provided. In one embodiment, artificial loci including at least one human C gene are used, and animals capable of producing antibodies having a human idiotype and human constant region are provided.

In another preferred embodiment, the transgenic animals carry at least one artificial Ig heavy chain locus, and lack a functional Ig light chain locus. Such animals find use in the production of heavy chain-only antibodies.

Production of such transgenic animals involves the integration of one or more artificial heavy chain Ig loci and one or more artificial light chain Ig loci into the genome of a transgenic animal having at least one endogenous Ig locus that has been or will be inactivated by the action of one or more meganucleases. Preferably, the transgenic animals are nullizygous for endogenous Ig heavy chain and/or endogenous Ig light chain and, accordingly, incapable of producing endogenous immunoglobulins. Regardless of the chromosomal location, an artificial Ig locus of the present invention has the capacity to undergo gene rearrangement and thereby produce a diversified repertoire of immunoglobulin molecules. An Ig locus having the capacity to undergo gene rearrangement is also referred to herein as a "functional" Ig locus, and the antibodies with a diversity generated by a functional Ig locus are also referred to herein as "functional" antibodies or a "functional" repertoire of antibodies.

The artificial loci used to generate such transgenic animals each include multiple immunoglobulin gene segments, which include at least one V region gene segment, one or more J gene segments, one or more D gene segments in the case of a heavy chain locus, and one or more constant region genes. In the present invention, at least one of the V gene segments encodes a germline or hypermutated human V-region amino acid sequence. Accordingly, such transgenic animals have the capacity to produce a diversified repertoire of immunoglobulin molecules, which include antibodies having a human idiotype.

In one embodiment, the artificial loci used comprise at least one non-human C region gene segment. Accordingly, such transgenic animals have the capacity to produce a diversified repertoire of immunoglobulin molecules, which include chimeric antibodies having a human idiotype.

In one embodiment, the artificial loci used comprise at least one human C region gene segment. Accordingly, such transgenic animals have the capacity to produce a diversified repertoire of immunoglobulin molecules, which include antibodies having a human idiotype and a human constant region.

In one embodiment, the artificial loci used comprise at least one artificial constant region gene. For example, an exemplary artificial C constant region gene is a constant region gene encoding a human IgG CH1 domain and rat IgG CH2 and CH3 domain. Accordingly, such transgenic animals have the capacity to produce a diversified repertoire of immunoglobulin molecules, which include antibodies having a human idiotype and an artificial constant region comprising both human and non-human components.

The transgenic vector containing an artificial Ig locus is introduced into the recipient cell or cells and then integrated into the genome of the recipient cell or cells by random integration or by targeted integration.

For random integration, a transgenic vector containing an artificial Ig locus can be introduced into a recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells or other pluripotent cells (for example primordial germ cells) and subsequently injecting the genetically modified cells into developing embryos. Alternatively, a transgenic vector (naked or in combination with facilitating reagents) can be directly injected into a developing embryo. Ultimately, chimeric transgenic animals are produced from the embryos which contain the artificial Ig transgene integrated in the genome of at least some somatic cells of the transgenic animal. In another embodiment, the transgenic vector is introduced into the genome of a cell and an animal is derived from the transfected cell by nuclear transfer cloning.

In a preferred embodiment, a transgene containing an artificial Ig locus is randomly integrated into the genome of recipient cells (such as fertilized oocyte or developing embryos). In a preferred embodiment, offspring that are nullizygous for endogenous Ig heavy chain and/or Ig light chain and, accordingly, incapable of producing endogenous immunoglobulins and capable of producing transgenic immunoglobulins are obtained.

For targeted integration, a transgenic vector can be introduced into appropriate recipient cells such as embryonic stem cells, other pluripotent cells or already differentiated somatic cells. Afterwards, cells in which the transgene has integrated into the animal genome can be selected by standard methods. The selected cells may then be fused with enucleated nuclear transfer unit cells, e.g. oocytes or embryonic stem cells, cells which are totipotent and capable of forming a functional neonate. Fusion is performed in accordance with conventional techniques which are well established. See, for example, Cibelli et al., Science (1998) 280:1256; Zhou et al. Science (2003) 301: 1179. Enucleation of oocytes and nuclear transfer can also be performed by microsurgery using injection pipettes. (See, for example, Wakayama et al., Nature (1998) 394:369.) The resulting cells are then cultivated in an appropriate medium, and transferred into synchronized recipients for generating transgenic animals. Alternatively, the selected genetically modified cells can be injected into developing embryos which are subsequently developed into chimeric animals.

In one embodiment, a meganuclease is used to increase the frequency of homologous recombination at a target site through double-strand DNA cleavage. For integration into a specific site, a site specific meganuclease may be used. In one embodiment, a meganuclease targeting an endogenous Ig locus is used to increase the frequency of homologous recombination and replacement of an endogenous Ig locus, or parts thereof with an artificial Ig locus, or parts thereof. In one embodiment, the transgenic animal lacks a functional Ig light chain locus and comprises an artificial Ig heavy chain locus.

Immunoglobulins Having a Human Idiotype

Once a transgenic animal capable of producing immunoglobulins having a human idiotype is made, immunoglobulins and antibody preparations against an antigen can be readily obtained by immunizing the animal with the antigen. "Polyclonal antisera composition" as used herein includes affinity purified polyclonal antibody preparations.

A variety of antigens can be used to immunize a transgenic animal. Such antigens include but are not limited to, microorganisms, e.g. viruses and unicellular organisms (such as bacteria and fungi), alive, attenuated or dead, fragments of the microorganisms, or antigenic molecules isolated from the microorganisms.

Preferred bacterial antigens for use in immunizing an animal include purified antigens from *Staphylococcus aureus* such as capsular polysaccharides type 5 and 8, recombinant versions of virulence factors such as alpha-toxin, adhesin binding proteins, collagen binding proteins, and fibronectin binding proteins. Preferred bacterial antigens also include an attenuated version of *S. aureus, Pseudomonas aeruginosa, enterococcus, enterobacter*, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa, enterococcus, enterobacter*, and *Klebsiella pneumoniae*.

Preferred antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans*.

Preferred antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatits B virus (HBV), cytomegalovirus (CMV), EBV, and HSV.

Antibodies specific for cancer can be generated by immunizing transgenic animals with isolated tumor cells or tumor cell lines as well as tumor-associated antigens which include, but are not limited to, Her-2-neu antigen (antibodies against which are useful for the treatment of breast cancer); CD20, CD22 and CD53 antigens (antibodies against which are useful for the treatment of B cell lymphomas), prostate specific membrane antigen (PMSA) (antibodies against which are useful for the treatment of prostate cancer), and 17-1A molecule (antibodies against which are useful for the treatment of colon cancer).

The antigens can be administered to a transgenic animal in any convenient manner, with or without an adjuvant, and can be administered in accordance with a predetermined schedule.

For making a monoclonal antibody, spleen cells are isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", J Immunol Methods 242:159 (2000), and by Burton, D. R., "Phage display", Immunotechnology 1:87 (1995).

Once chimeric monoclonal antibodies with human idiotypes have been generated, such chimeric antibodies can be easily converted into fully human antibodies using standard molecular biology techniques. Fully human monoclonal antibodies are not immunogenic in humans and are appropriate for use in the therapeutic treatment of human subjects.

Antibodies of the Invention Include Heavy Chain-Only Antibodies

In one embodiment, transgenic animals which lack a functional Ig light chain locus, and comprising an artificial heavy chain locus, are immunized with antigen to produce heavy chain-only antibodies that specifically bind to antigen.

In one embodiment, the invention provides monoclonal antibody producing cells derived from such animals, as well as nucleic acids derived therefrom. Also provided are hybridomas derived therefrom. Also provided are fully human heavy chain-only antibodies, as well as encoding nucleic acids, derived therefrom.

Teachings on heavy chain-only antibodies are found in the art. For example, see PCT publications WO02085944, WO02085945, WO2006008548, and WO2007096779. See also U.S. Pat. No. 5,840,526; U.S. Pat. No. 5,874,541; U.S. Pat. No. 6,005,079; U.S. Pat. No. 6,765,087; U.S. Pat. No. 5,800,988; EP 1589107; WO 9734103; and U.S. Pat. No. 6,015,695.

Pharmaceutical Compositions

In a further embodiment of the present invention, purified monoclonal or polyclonal antibodies are admixed with an appropriate pharmaceutical carrier suitable for administration to patients, to provide pharmaceutical compositions.

Patients treated with the pharmaceutical compositions of the invention are preferably mammals, more preferably humans, though veterinary uses are also contemplated.

Pharmaceutically acceptable carriers which can be employed in the present pharmaceutical compositions can be any and all solvents, dispersion media, isotonic agents and the like. Except insofar as any conventional media, agent, diluent or carrier is detrimental to the recipient or to the therapeutic effectiveness of the antibodies contained therein, its use in the pharmaceutical compositions of the present invention is appropriate.

The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

Methods of Treatment

In a further aspect of the present invention, methods are provided for treating a disease in a vertebrate, preferably a mammal, preferably a primate, with human subjects being an especially preferred embodiment, by administering a purified antibody composition of the invention desirable for treating such disease.

The antibody compositions can be used to bind and neutralize or modulate an antigenic entity in human body tissues that causes or contributes to disease or that elicits undesired or abnormal immune responses. An "antigenic entity" is herein defined to encompass any soluble or cell surface bound molecules including proteins, as well as cells or infectious disease-causing organisms or agents that are at least capable of binding to an antibody and preferably are also capable of stimulating an immune response.

Administration of an antibody composition against an infectious agent as a monotherapy or in combination with chemotherapy results in elimination of infectious particles. A single administration of antibodies decreases the number of infectious particles generally 10 to 100 fold, more commonly more than 1000-fold. Similarly, antibody therapy in patients with a malignant disease employed as a monotherapy or in combination with chemotherapy reduces the number of malignant cells generally 10 to 100 fold, or more than 1000-fold. Therapy may be repeated over an extended amount of time to assure the complete elimination of infectious particles, malignant cells, etc. In some instances, therapy with antibody preparations will be continued for extended periods of time in the absence of detectable amounts of infectious particles or undesirable cells.

Similarly, the use of antibody therapy for the modulation of immune responses may consist of single or multiple administrations of therapeutic antibodies. Therapy may be continued for extended periods of time in the absence of any disease symptoms.

The subject treatment may be employed in conjunction with chemotherapy at dosages sufficient to inhibit infectious disease or malignancies. In autoimmune disease patients or transplant recipients, antibody therapy may be employed in conjunction with immunosuppressive therapy at dosages sufficient to inhibit immune reactions.

Examples

In mice transgenic for human immunoglobulin (Ig) loci, suboptimal efficacy in delivery of fully human antibodies has been attributed to imperfect interaction between the constant regions of human membrane IgH chains and the mouse cellular signaling machinery. To obviate this problem, we here describe a humanized rat strain (OmniRat™) carrying a chimeric human/rat IgH locus [comprising 22 human $V_H$s, all human D and $J_H$ segments in natural configuration but linked to the rat $C_H$ locus] together with fully human light-chain loci [12 Vκs linked to Jκ-CK and 16 Vλs linked to Jλ-Cλ]. The endogenous rat Ig loci were silenced by designer zinc finger nucleases. Following immunization, OmniRats perform as efficiently as normal rats in yielding high affinity serum IgG. Monoclonal antibodies, comprising fully human variable regions with sub-nanomolar antigen affinity and carrying extensive somatic mutations, are readily obtainable—similarly to the yield of conventional antibodies from normal rats.

Materials and Methods

Construction of Modified Human Ig Loci on YACs and BACs a) IgH Loci

The human IgH V genes were covered by 2 BACs: BAC6-VH3-11 containing the authentic region spanning from VH4-39 to VH3-23 followed by VH3-11 (modified from a commercially available BAC clone 3054M17 CITB) and BAC3 containing the authentic region spanning from VH3-11 to VH6-1 (811L16 RPCI-11). A BAC termed Annabel was constructed by joining rat CH region genes immediately downstream of the human VH6-1-Ds-JHs region (FIG. 1). All BAC clones containing part of the human or rat IgH locus were purchased from Invitrogen.

Both BAC6-VH3-11 and Annabel were initially constructed in S. cerevisiae as circular YACs (cYACs) and further checked and maintained in E. coli as BACs. Construction details can be found at www.ratltd.net.

Unlike YACs, BAC plasmid preps yield large quantities of the desired DNA. To convert a linear YAC into a cYAC or to assemble DNA fragments with overlapping ends into a single cYAC in S. cerevisiae, which can also be maintained as a BAC in E. coli, two self-replicating S. cerevisiae/E. coli shuttle vectors, pBelo-CEN-URA, and pBelo-CEN-HYG were constructed. Briefly, S. cerevisiae CEN4 was cut out as an AvrII fragment from pYAC-RC[39] and ligated to SpeI— linearised pAP599[40]. The resulting plasmid contains CEN4 cloned in between S. cerevisiae URA3 and a hygromycin-resistance expression cassette (HygR). From this plasmid, an ApaLI-BamHI fragment containing URA3 followed by CEN4 or a PmlI-SphI fragment containing CEN4 followed by HygR was cut out, and ligated to ApaLI and BamHI or HpaI and SphI doubly digested pBACBelo11 (New England Biolabs) to yield pBelo-CEN-URA and pBelo-CEN-HYG.

To construct BAC6-VH3-11, initially two fragments, a 115 kb NotI-PmeI and a 110 kb RsrII-SgrAI, were cut out from the BAC clone 3054M17 CITB. The 3' end of the former fragment overlaps 22 kb with the 5' end of the latter. The NotI-PmeI fragment was ligated to a NotI-BamHI YAC arm containing S. cerevisiae CEN4 as well as TRP1/ARS1 from pYAC-RC, and the RsrII-SgrAI fragment was ligated to a SgrAI-BamHI YAC arm containing S. cerevisiae URA3, also from pYAC-RC. Subsequently, the ligation mixture was transformed into S. cerevisiae AB1380 cells via spheroplast transformation[41], and URA+TRP+ yeast clones were selected. Clones, termed YAC6, containing the linear region from human VH4-39 to VH3-23 were confirmed by Southern blot analysis. YAC6 was further extended by addition of a 10.6 kb fragment 3' of VH3-23, and conversion to a cYAC. The 10.6 kb extension contains the human VH3-11 and also occurs at the 5' end of BAC3. We constructed pBeloHYG-YAC6+BAC3(5') for the modification of YAC6. Briefly, 3 fragments with overlapping ends were prepared by PCR: 1) a 'stuff' fragment containing S. cerevisiae TRP1-ARS1 flanked by HpaI sites with 5' tail matching the sequence upstream of VH4-39 and 3' tail matching downstream of VH3-23 in YAC6 (using long oligoes 561 and 562, and pYAC-RC as template), 2) the 10.6 kb extension fragment with a 5' tail matching the sequence downstream of VH3-23 as described above and a unique AscI site at its 3' end (using long oligoes 570 and 412, and human genomic DNA as template), and 3) pBelo-CEN-HYG vector with the CEN4 joined downstream with a homology tail matching the 3' end of the 10.6 extension fragment and the HygR joined upstream with a tail matching the sequence upstream of VH4-39 as described above (using long oligoes 414 and 566, and pBelo-CEN-HYG as template). Subsequently, the 3 PCR fragments were assembled into a small cYAC conferring HYGR and TRP+ in S. cerevisiae via homologous recombination associated with spheroplast transformation, and this cYAC was further converted into the BAC pBeloHYG-YAC6+BAC3(5'). Finally, the HpaI-digested pBeloHYG-YAC6+BAC3(5') was used to transform yeast cells carrying YAC6, and through homologous recombination cYAC BAC6-VH3-11 conferring only HYGR was generated. Via transformation, see below, this cYAC was introduced as a BAC in E. coli. The human VH genes in BAC6-VH3-11 were cut out as a ~182 kb AsiSI (occurring naturally in the HygR)—AscI fragment, and the VH genes in BAC3 were cut out as a ~173 kb NotI-fragment (FIG. 1 top).

For the assembly of the C region with the VH overlap, the human VH6-1-Ds-JHs region had to be joined with the rat genomic sequence immediately downstream of the last JH followed by rat Cs to yield a cYAC/BAC. To achieve this, 5 overlapping restriction as well as PCR fragments were prepared; a 6.1 kb fragment 5' of human VH6-1 (using oligoes 383 and 384, and human genomic DNA as template), an ~78 kb PvuI-PacI fragment containing the human VH6-1-Ds-JHs region cut out from BAC1 (RP11645E6), a 8.7 kb fragment joining the human JH6 with the rat genomic sequence immediately downstream of the last JH and containing part of rat μ coding sequence (using oligos 488 and 346, and rat genomic DNA as template), an ~52 kb NotI-PmeI fragment containing the authentic rat μ, δ and γ2c region cut out from BAC M5 (CH230-408M5) and the pBelo-CEN-URA vector with the URA3 joined downstream with a homology tail matching the 3' end of the rat γ2c region and the CEN4 joined upstream with a tail matching the 5' region of human VH6-1 as described (using long oligoes 385 and 550, and pBelo-CEN-URA as template). Correct assembly via homologous recombination in S. cerevisiae was analysed by PCR and purified cYAC from the correct clones was converted into a BAC in E. coli.

For the assembly of Annabel parts of the above cYAC/BAC containing humanVH6-1-Ds-JHs followed by the authentic rat μ, δ and γ2c region, as well as PCR fragments were used. Five overlapping fragments contained the 6.1 kb fragment at the 5' end of human VH6-1 as described above, an ~83 kb SpeI fragment comprising human VH6-1-Ds-JHs immediately followed by the rat genomic sequence downstream of the last JH and containing part of rat Cμ, a 5.2 kb fragment joining the 3' end of rat μ with the 5' end of rat γ1 (using oligos 490 and 534, and rat genomic DNA as template), an ~118 kb NotI-SgrAI fragment containing the authentic rat γ1, γ2b, ε, α and 3'E IgH enhancer region cut out from BAC 18 (CH230-162I08), and the pBelo-CEN-URA vector with the URA3 joined downstream with a homology tail matching the 3' end of rat 3'E and the CEN4 joined upstream with a tail matching the 5' end of human VH6-1 as described above. There is a 10.3 kb overlap between the human VH6-1 regions in both the BAC3 and Annabel. The human VH6-1-Ds-JHs followed by the rat CH region together with the S. cerevisiae URA3 in Annabel can be cut out as a single ~183 kb NotI-fragment (see FIG. 1 top).

BAC6-VH3-11, BAC3 and Annabel were checked extensively by restriction analysis and partial sequencing for their authenticity.

b) IgL Loci

The human Igk locus on a ~410 kb YAC was obtained by recombination assembly of a Vλ YAC with 3 Cλ containing cosmids[25]. Rearrangement and expression was verified in transgenic mice derived from ES cells containing one copy of a complete human Igλ YAC[38]. This Igλ YAC was shortened by the generation of a circular YAC removing ~100 kb of the region 5' of Vλ3-27. The vector pYAC-RC was digested with ClaI and BspEI to remove URA3 and ligated with a ClaI/NgoMIV fragment from pAP 599 containing HYG. PCR of the region containing the yeast centromere and hygromycin marker gene from the new vector (pYAC-RC-HYG) was carried out with primers with 5' ends homologous to a region 5' of Vλ3-27 (primer 276) and within the ADE2 marker gene in the YAC arm (primer 275). The PCR fragment (3.8 kb) was integrated into the Igλ YAC using a high efficiency lithium acetate transformation method[42] and selection on hygromycin containing YPD plates. DNA was prepared from the clones (Epicentre MasterPure Yeast DNA purification kit) and analysed for the correct junctions by PCR using the following oligos: 243+ 278 and Hyg end R+238. Plugs were made[43] and yeast chromosomes removed by PFGE (0.8% agarose (PFC) (Biorad) gel [6V/cm, pulse times of 60 s for 10 hr and 10 s for 10 hr, 8° C.) leaving the circular yeast artificial chromosome caught in the agarose block[44]. The blocks were removed and digested with NruI. Briefly, blocks were pre-incubated with restriction enzyme buffer in excess at a 1× final concentration for 1 hr on ice. Excess buffer was removed leaving just enough to cover the plugs, restriction enzyme was added to a final concentration of 100 U/ml and the tube incubated at 37° C. for 4-5 hrs. The linearized YAC was ran out of the blocks by PFGE, cut out from the gel as a strip and purified as described below.

For the human Igκ locus 3 BACs were chosen (RP11-344F17, RP11-1134E24 and RP11-156D9, Invitrogen), which covered a region over 300 kb from 5' Vκ1-17 to 3' KDE[45]. In digests and sequence analyses three overlapping fragments were identified: from Vκ1-17 to Vκ3-7 (150 kb NotI with ~14 kb overlap), from Vκ3-7 to 3' of Cκ (158 kb NotI with ~40 kb overlap) and from Cκ to 3' of the KDE (55 kb PadI with 40 kb overlap). Overlapping regions may generally favour joint integration when co-injected into oocytes[24].

Gel Analyses and DNA Purification

Purified YAC and BAC DNA was analysed by restriction digest and separation on conventional 0.7% agarose gels[46]. Larger fragments, 50-200 kb, were separated by PFGE (Biorad Chef Mapper™) at 80 C, using 0.8% PFC Agaraose in 0.5% TBE, at 2-20 sec switch time for 16 h, 6V/cm, 10 mA. Purification allowed a direct comparison of the resulting fragments with the predicted size obtained from the sequence analysis. Alterations were analysed by PCR and sequencing.

Linear YACs, circular YACs and BAC fragments after digests, were purified by electro-elution using Elutrap™ (Schleicher and Schuell)[47] from strips cut from 0.8% agarose gels run conventionally or from pulsed-field-gel electrophoresis (PFGE). The DNA concentration was usually several ng/μl in a volume of ~100 μl. For fragments up to ~200 kb the DNA was precipitated and re-dissolved in micro-injection buffer (10 mM Tris-HCl pH 7.5, 100 mM EDTA pH 8 and 100 mM NaCl but without Spermine/Spermidine) to the desired concentration.

The purification of circular YACs from yeast was carried out using Nucleobond AX silica-based anion-exchange resin (Macherey-Nagel, Germany). Briefly, spheroplasts were made using zymolyase or lyticase and pelleted[20]. The cells then underwent alkaline lysis, binding to AX100 column and elution as described in the Nucleobond method for a low-copy plasmid. Contaminating yeast chromosomal DNA was hydrolyzed using Plamid-Safe™ ATP-Dependent DNase (Epicentre Biotechnologies) followed by a final cleanup step using SureClean (Bioline). An aliquot of DH10 electrocompetent cells (Invitrogen) was then transformed with the circular YAC to obtain BAC colonies. For microinjection, the insert DNA (150-200 kb), was separated from BAC vector DNA (~10 kb) using a filtration step with sepharose 4B-CL[48].

Derivation of Rats and Breeding

Purified DNA encoding recombinant immunoglobulin loci was resuspended in microinjection buffer with 10 mM Spermine and 10 mM Spemidine. The DNA was injected into fertilized oocytes at various concentrations from 0.5 to 3 ng/μl.

Plasmid DNA or mRNA encoding ZFNs specific for rat immunoglobulin genes were injected into fertilized oocytes at various concentrations from 0.5 to 10 ng/ul.

Microinjections were performed at Caliper Life Sciences facility. Outbred SD/Hsd (WT) strain animals were housed in standard microisolator cages under approved animal care protocols in animal facility that is accredited by the Association for the Assessment and Accreditation for Laboratory Animal Care (AAALAC). The rats were maintained on a 14-10 h light/dark cycle with ad libitum access to food and water. Four to five week old SD/Hsd female rats were injected with 20-25 IU PMSG (Sigma-Aldrich) followed 48 hours later with 20-25 IU hCG (Sigma-Aldrich) before breeding to outbred SD/Hsd males. Fertilized 1-cell stage embryos were collected for subsequent microinjection. Manipulated embryos were transferred to pseudopregnant SD/Hsd female rats to be carried to parturition.

Multi-feature human Ig rats (human IgH, Igκ and Igλ in combination with rat J KO, κ KO and κ KO) and WT, as control, were analyzed at 10-18 weeks of age. The animals were bred at Charles River under specific pathogen-free conditions.

PCR and RT-PCR

Transgenic rats were identified by PCR from tail or ear clip DNA using a Genomic DNA Mini Kid (Bioline). For IgH PCRs<1 kb GoTaq Green Master mix was used (Promega) under the following conditions: 94° C. 2 mins, 32×(94° C. 30 secs, 54-670 C (see supplemental Table 1 for primers and specific annealing temperatures) 30 secs, 72° C. 1 min), 72° C. 2 mins. For IgH PCRs>1 kb KOD polymerase (Novagen) was used under the following conditions: 95° C. 2 mins, 32×(95° C. 20 secs, 56-620 C (supplementary Table 1) 20 secs, 70° C. 90 secs), 70° C. 2 mins. For Igκ and Igλ PCR, all <1 kb, the above condition were used except extension at 72° C. for 50 secs.

RNA was extracted from Blood using the RiboPure Blood Kit (Ambion) and RNA extraction from spleen, bone marrow or lymph nodes used RNASpin mini kit. (GE Healthcare). cDNA was made using Oligo dT and Promega Reverse Transcriptase at 42° C. for 1 hour. GAPDH PCR reactions (oligos 429-430) determined the concentration.

RT-PCRs were set up using VH leader primers with rat μCH2 or rat γCH2 primers (supplementary Table 1). Amplification with GoTaq Green Master mix were 94° C. 2 mins, 34×(94° C. 30 secs, 55-65° C. 30 secs, 72° C. 50-60 secs), 72° C. 2 mins. PCR products of the expected size were either purified by gel or QuickClean (Bioline) and sequenced directly or cloned into pGemT (Promega).

Protein Purification

IgM was purified on anti-IgM affinity matrix (BAC B.V., Netherlands, CaptureSelect #2890.05) as described in the protocol. Similarly, human Igκ and Igλ was purified on anti-L chain affinity matrix (CaptureSelect anti-Igκ #0833 and anti-Igλ #0849) according to the protocol.

For rat IgG purification[29] protein A and protein G agarose was used (Innova, Cambridge, UK, #851-0024 and #895-0024). Serum was incubated with the resin and binding facilitated at 0.1 M sodium phosphate pH 7 for protein G and pH 8 for protein A under gentle mixing. Poly-prep columns (Bio-Rad) were packed with the mixture and washed extensively with PBS pH7.4. Elution buffer was 0.1 M Sodium Citrate pH 2.5 and neutralization buffer was 1 M Tris-HCl pH 9

Electrophoresis was performed on 4-15% SDS-PAGE and Coomassie brilliant blue was used for staining MW standards were HyperPage Prestained Protein Marker (#BIO-33066, Bioline).

Flow Cytometry Analysis and FISH

Cell suspensions were washed and adjusted to 5×105 cells/100 µl in PBS-1% BSA-0.1% Azide. Different B-cell subsets were identified using mouse anti-rat IgM FITC-labelled mAb (MARM 4, Jackson Immunoresearch Laboratories) in combination with anti-B cell CD45R (rat B220)-PE-conjugated mAb (His 24, BD biosciences) or anti-IgD-PE-conjugated mAb (MARD-3, Abd Serotec). A FACS Cantoll flow cytometer and FlowJo software (Becton Dickinson, Pont de Claix, France) was used for the analysis.

Fluorescence in situ hybridisation was carried out on fixed blood lymphocytes using purified IgH and IgL C-region BACs as described.[49]

Immunization, Cell Fusion and Affinity Measurement

Immunizations were performed with 125 µg PG in CFA, 150 µg hGHR in CFA, 200 µg Tau/KLH in CFA, 150 µg HEL in CFA, 150 µg OVA in CFA at the base of the tail and medial iliac lymph node cells were fused with mouse P3X63Ag8.653 myeloma cells 22 days later as described[50]. For multiple immunizations protein, 125 µg PG or HEL, or 100 µg hGHR or CD14 in GERBU adjuvant (www.Gerbu.com), was administered intraperitoneally as follows: day 0, day 14, day 28 and day 41 without adjuvant, followed by spleen cell fusion with P3x63Ag8.653 cells 4 days later.[49]

Binding kinetics were analyzed by surface Plasmon resonance using a Biacore 2000 with the antigens directly immobilized as described[23].

SUPPLEMENTARY TABLE 1

PCR* and RT-PCR** conditions to detect human IgH and IgL integration and expression

|  | Primers | Annealing Temp (Tm-5) | Fragment size |
|---|---|---|---|
| IgH |  |  |  |
| Hyg (5' BAC6) | Hyg 3' F - 459 | 54° C. | ~400 bp |
| V4-34 (BAC6) | 205-206 | 65° C. | ~1 kb |
| V4-28 (BAC6) | 203-204 | 65° C. | ~1 kb |
| V3-11 (overlap BAC6-BAC3) | 448-461 | 60° C. | ~500 bp |
| V1-8 (BAC3) | 371-372 | 60° C. | ~300 bp |
| V4-4 (BAC3) | 393-396 | 60° C. | ~750 bp |
| V6-1 (BAC3-Annabel) | 359-360 | 65° C. | ~350 bp |
| JH (Annabel) | 368-369 | 62° C. | ~250 bp |
| µ-γ1 (Annabel) | 583-535 | 62° C. | ~3 kb |
| Ura (3' Annabel) | 241-253 | 56° C. | ~3 kb |
| Igκ |  |  |  |
| KDE | 313-314 | 66° C. | ~600 bp |
| cKappa | 307-308 | 64° C. | ~600 bp |
| V4-1 | 333-334 | 60° C. | ~300 bp |
| V1-5 | 329-330 | 64° C. | ~400 bp |
| V1-6 | 331-332 | 60° C. | ~300 bp |
| V3-7 | 309-310 | 66° C. | ~700 bp |
| V3-15 | 311-312 | 66° C. | ~500 bp |
| Igλ |  |  |  |
| V3-27 | 215-216 | 67° C. | ~400 bp |
| V3-19 | 213-214 | 67° C. | ~700 bp |
| V2-14 | 211-212 | 67° C. | ~400 bp |
| V middle | 168-169 | 65° C. | ~500 bp |
| JLambda | 162-163 | 67° C. | ~800 bp |
| cLambda | 170-171 | 67° C. | ~500 bp |
| Enhancer | 172-173 | 67° C. | ~400 bp |

SUPPLEMENTARY TABLE 1-continued

PCR* and RT-PCR** conditions to detect human IgH and IgL integration and expression

|  | Primer | Annealing Temp (Tm-5) | Fragment size |
|---|---|---|---|
| IgH |  |  |  |
| VH1 Leader | 390 | 65° C. | ↓ |
| VH2 Leader | 391 | 65° C. | ↓ |
| VH3 Leader | 392 | 65° C. | ↓ |
| VH4 Leader | 393 | 60° C. | ↓ |
| VH6 Leader | 394 | 65° C. | ↓ |
| VH4-39 Leader | 761 | 55° C. | ↓ |
| Rat µCH2 | 345 | ↑ | ~1 kb |
| Rat □CH2 | 682 | ↑ | ~800 bp |
| Ig□ |  |  |  |
| HuVK1 Leader | 400/474 | 63° C. | ↓ |
| HuVK3 Leader | 401/475 | 63° C. | ↓ |
| HuVK4 Leader | 476 | 63° C. | ↓ |
| HuVK5 Leader | 477 | 63° C. | ↓ |
| Hu □ C region | 402 | ↑ | ~600 bp |
| HuVL2 Leader | 388/478 | 58° C. | ↓ |
| HuVL3 Leader | 398/479/480/482/ 483/481/484 | 58° C. | ↓ |
| HuVL4 Leader | 485 | 58° C. | ↓ |
| Hu □ □C region | 387 | ↑ | ~600 bp |

*For DNA extraction from ear and tail clips the Genomic DNA Mini Kit (Bioline) was used. For PCRs 1 kb or less in size GoTaq Green Master mix (Promega) was used under the following conditions: 94° C. 2 mins, 32 × (94° C. 30 secs, Tm-5 (below) 30 secs, 72° C. 1 min [50 sec for Igκ/λ]), 72° C. 2 mins. Annealing temperatures were set at the lowest primer Tm-5° C. (www.sigmagenosys.com/calc/DNACalc.asp). For PCRs > 1 kb KOD polymerase (Novagen) was used under the following conditions: 95° C. 2 mins, 32 × (95° C. 20 secs, Tm-5 20 secs, 70° C. 90 secs), 70° C. 2 mins.
**RNA was extracted from Blood using the RiboPure Blood Kit (Ambion). RNA extracted from spleen, bone marrow or lymph nodes used the RNASpin mini kit (GE Healthcare). cDNA was made using Oligo dT and Promega Reverse Transcriptase at 42° C. 1 hour. PCRs using the GoTaq Green Master mix were set up as follows: 94° C. 2 mins, 34 × (94° C. 30 secs, Tm-5 30 secs, 72° C. 1 min [50 sec for Igκ/λ]), 72° C. 2 mins.

Primers

| Number | Oligonucleotide sequence 5'-3' |
|---|---|
| 162 | GGGGCCAAGGCCCCGAGAGATCTCAGG |
| 163 | CACTGGGTTCAGGGTTCTTTCCACC |
| 168 | GTGGTACAGAAGTTAGAGGGGATGTTGTTCC |
| 169 | TCTTCTACAAGCCCTTCTAAGAACACCTGG |
| 170 | AGCACAATGCTGAGGATGTTGCTCC |
| 171 | ACTGACCCTGATCCTGACCCTACTGC |
| 172 | AAACACCCCTCTTCTCCCACCAGC |
| 173 | CGCTCATGGTGAACCAGTGCTCTG |
| 203 | GCTATTTAAGACCCACTCCCTGGCA |
| 204 | AAAACCTGCAGCAAGGATGTGAGG |
| 205 | GCTCCTTCAGCACATTTCCTACCTGGA |
| 206 | CCATATATGGCAAAATGAGTCATGCAGG |
| 211 | CTCTGCTGCTCCTCACCCTCCTCACTCAGG |
| 212 | GAGAGTGCTGCTGCTTGTATATGAGCTGCA |
| 213 | TGGCTCACTCTCCTCACTCTTTGCATAGGTT |
| 214 | GATGGTTACCACTGCTGTCCCGGGAGTTAC |
| 215 | ATCCCTCTCCTGCTCCCCTCCTCATTCTCTG |
| 216 | TGATGGTCAAGGTGACTGTGGTCCCTGAGCTG |

| Number | Oligonucleotide sequence 5'-3' |
|---|---|
| 238 | AACAAGTGCGTGGAGCAG |
| 241 | GTACTGTTGACATTGCGAAGAGC |
| 243 | TGGTTGACATGCTGGCTAGTC |
| 253 | TGTCTGGCTGGAATACACTC |
| 275 | AAATGAGCTTCAAATTGAGAAGTGACGCAAGCATCAATGGTATAATGTCCAGAGTTGTGAGGCCTTGGGGACTGTGTGCCGAACATGCTC |
| 276 | CCAGCACTGTTCAATCACAGTATGATGAGCCTAATGGGAATCCCACTAGGCTAGTCTAGTCACCACATTAAAGCACGTGGCCTCTTATCG |
| 278 | TGACCATTGCTTCCAAGTCC |
| 307 | GAGGAAAGAGAGAAACCACAGGTGC |
| 308 | CACCCAAGGGCAGAACTTTGTTACT |
| 309 | TGTCCAGGTATGTTGAAGAATGTCCTCC |
| 310 | TGGACTCTGTTCAACTGAGGCACCAG |
| 311 | GGCCTTCATGCTGTGTGCAGACTA |
| 312 | CAGGTCGCACTGATTCAAGAAGTGAGT |
| 313 | TTCAGGCAGGCTCTTACCAGGACTCA |
| 314 | TGCTCTGACCTCTGAGGACCTGTCTGTA |
| 329 | TCACGTGACTGTGATCCCTAGAA |
| 330 | CACTGTTATGCCAACTGAACAGC |
| 331 | CGTAGCAGTCCCCATCTGTAATC |
| 332 | ATGTCAGAGGAGCAGGAGAGAGA |
| 333 | CACGCCTCACATCCAATATGTTA |
| 334 | ATACCCTCCTGACATCTGGTGAA |
| 345 | GCTTTCAGTGATGGTCAGTGTGCTTATGAC |
| 346 | TGGAAGACCAGGAGATATTCAGGGTGTC |
| 359 | TTGCTTAACTCCACACCTGCTCCTG |
| 360 | TGCTTGGAACTGGATCAGGCAGTC |
| 368 | CACCCTGGTCACCGTCTCC |
| 369 | AGACAGTGACCAGGGTGCCAC |
| 371 | TGAGGAACGGATCCTGGTTCAGTC |
| 372 | ATCTCCTCAGCCCAGCACAGC |
| 383 | CCTCCCATGATTCCAACACTG |
| 384 | CTCACCGTCCACCACTGCTG |
| 385 | CTGTGCCACAAACATGCAAAGATAAGTTCCATGTGACAAGTCTGAACTCAGTGTTGGAATCATGGGAGGCGGCCGCGTTATCTATGCTGTCTCACCATAG |
| 387 | TGCTCAGGCGTCAGGCTCAG |
| 388 | TGCTCAGGCGTCAGGCTCAG |
| 390 | ATGGACTGGACCTGGAGGATCC |
| 391 | TCCACGCTCCTGCTGCTGAC |
| 392 | ATGGAGTTTGGGCTGAGCTGG |
| 393 | TGAAACACCTGTGGTTCTTCC |
| 394 | TCATCTTCCTGCCCGTGCTGG |
| 396 | GACTCGACTCTTGAGGGACG |
| 398 | ATGTGGCCACAGGCTAGCTC |
| 400 | ATGAGGGTCCCCGCTCAG |
| 401 | ATGGAAGCCCCAGCTCAGC |
| 402 | CCTGGGAGTTACCCGATTGG |
| 412 | GGCGCGCCAAGCATCATGTCCTACCTGGCTG |
| 414 | CAAAGTACGTGGCACCTCCCTCGTCTTTCTTCCTCCTGCTCCAGCCAGGTAGGACATGATGCTTGGCGCGCCGTTATCTATGCTGTCTCACCATAG |
| 429 | CAGTGCCAGCCTCGTCTCAT |
| 430 | AGGGGCCATCCACAGTCTTC |
| 448 | CTTCACTGTGTGTTCTTGGGATAC |
| 459 | GTGTAATGCTTTGGACGGTGTGTTAGTCTC |
| 461 | GCATAGCGGCGCGCCAAGCATCATGTCCTACCTGGCTG |
| 474 | GACATGAGAGTCCTCGCTCAGC |
| 475 | AAGCCCCAGCGCAGCTTC |
| 476 | ATGGTGTTGCAGACCCAGGTC |
| 477 | GTCCCAGGTTCACCTCCTCAG |
| 478 | TCCTCASYCTCCTCACTCAGG |
| 479 | CGTCCTTGCTTACTGCACAG |
| 480 | AGCCTCCTTGCTCACTTTACAG |
| 481 | CCTCCTCAYTYTCTGCACAG |
| 482 | GCTCACTCTCCTCACTCTTTGC |
| 483 | CCTCCTCTCTCACTGCACAG |
| 484 | GCCACACTCCTGCTCCCACT |
| 485 | ATGGCCTGGGTCTCCTTCTAC |
| 488 | ATTACTACTACTACTACATGGACGTCTGGGGCAAAGGGACCACGGTCACCGTCTCCTCAGGAAGAATGGCCTCTCCAGGTC |
| 490 | CTGTCGTTGAGATGAACCCCAATGTGAG |
| 534 | GGAACTGATGTGATCTCAGTCACACAGCTAATGCAAAGGTCAGCAGGCTGTTTACTGCCTGGAGGTTCATCGCCCAATTCCAAAGTCAC |
| 535 | CTAGTCTGCATGGGTCTCCGCAAAC |
| 550 | CTGGTATAATCATAAGTCTCCACTTAATAGTTCTGTAGACAGAATCTTCATTTAGACTTACAGACCGCGGCCGCACCGCAGGGTAATAACTG |

-continued

| Number | Oligonucleotide sequence 5'-3' |
|---|---|
| 561 | GCAACCCTTCTTGCCACTCATGTCCCAGCTCTCACCATGTGACATAGCCTGTTAACAATTCGGTCGAAAAAAGAAAAGGAGAG |
| 562 | AATGTTCTTAGTATATATAAACAAGCTACTCCAATTCATAGTCAACTAAGTTAACATTCCACATGTTAAAATAGTGAAGGAG |
| 566 | TTAACAGGCTATGTCACATGGTGAGAGCTGGGACATGAGTGGCAAGAAGGGTTGCCAGACTCCCCCTTTACCTCTATATCGTGTTC |
| 570 | CTTAGTTGACTATGAATTGGGAGTAGCTTGTTTATATATACTAAGAACATTTGTCAGAAGCTCTTTCTTGTTTATTCCCAGTTTGC |
| 583 | CATGTCCGTATGTTGCATCTGC |
| 682 | GGGAAGATGAAGACAGATG |
| 761 | TGGAGTGGATTGGGAGT |

Results

The Human IgH and IgL Loci

Construction of the human Ig loci employed established technologies to assemble large DNA segments using YACs and BACs[16, 19, 24-26]. As multiple BAC modifications in *E. coli* frequently deleted repetitive regions such as switch sequences and enhancers, a method was developed to assemble sequences with overlapping ends in *S. cerevisiae* as circular YAC (cYAC) and, subsequently, converting such a cYAC into a BAC. Advantages of YACs include their large size, the ease of homologous alterations in the yeast host and the sequence stability, while BACs propagated in *E. coli* offer the advantages of easy preparation and large yield. Additionally, detailed restriction mapping and sequencing analysis can be better achieved in BACs than in YACs.

Sequence analysis and digests identified gene clusters of interest and ensured locus integrity and functionality to secure DNA rearrangement and switching over a wide region. The layout of the human IgH (human VH, D and JH segments followed by rat C genes), Igκ and Igλ loci are depicted in FIG. 1a-c. As shown previously, overlapping regions may generally favor joint integration when co-injected into oocytes[24]. Thereby, insertion of BAC6-VH3-11, a 182 kb AsiSI-AscI fragment, with BAC3, a 173 kb NotI fragment, and BAC3-1N12M518 (Hu-Rat Annabel), a 193 kb NotI fragment, led to the reconstitution of a fully functional transgenic IgH loci in the rat genome. Similarly, the human Igκ locus was integrated by homologous overlaps. The human Igλ locus was isolated intact as a ~300 kb YAC and also fully inserted into a rat chromosome. The integration success was identified by transcript analysis which showed V(D)J-C recombinations from the most 5' to the most 3' end of the locus injected. Multiple copies were identified by qPCR (not shown) and it is likely that head to tail integrations occurred. In all cases, transgenic animals with single-site integrations were generated by breeding.

Breeding to Homozygosity

The derivation of transgenic rats by DNA microinjection into oocytes, their breeding and immunization is comparable to the mouse. However, ZFN technology to obtain gene knock-outs has only been reported recently[11, 13]. Silencing of the rat IgH locus by $J_H$ deletion using ZFN KO technology has been described[12] and a manuscript describing silencing of the rat IgL loci, targeting of Cκ and deletion of J-Cλ genes, is in preparation. We derived multiple founders with integrated human Ig loci and silenced endogenous Ig production; all analyzed by PCR and FISH with complete trans-locus integration selected and interbred (Table 2). Several founder rats carried low translocus copy numbers; with the rat C-gene BAC in OmniRat likely to be fully integrated in 5 copies as determined by qPCR of Cμ and Cα products (not shown). Identification by FISH of single position insertion in many lines confirmed that spreading or multiple integration of BAC mixtures were rare; an advantage for breeding to homozygosity, which was achieved.

TABLE 2

Generated rat lines: transgenic integration, knock-out and gene usage

| | human $V_H$ | | rat $C_H$ | human Igκ | human Igl | ZFN KO | | | FISH |
|---|---|---|---|---|---|---|---|---|---|
| | BAC6- | | | | | | | | |
| rat line | VH3-11 182 kb | BAC3 173 kb | (Annabel) 193 kb | BACs 300 kb | Igl YAC 300 kb | $J_H$ KO | Igκ KO | Igγ KO | rat chromosome |
| HC14 | ✓ | ✓ | ✓ | | | | | | 5q22 |
| OmniRat | ✓ | ✓ | ✓ | ✓ | ✓ | ✓ | ✓ | ✓ | homozygous KOs |
| LC#79 | | | | ✓ | | | | | 17 |
| LC#6.2 | | | | | ✓ | | | | 6q23 |
| #117 | | | | | | ✓ | | | 6q32 |
| #23 | | | | | | | ✓ | | 4 |
| #35 | | | | | | | | ✓ | 11 |

Rats carrying the individual human transloci—IgH, Igκ and Igλ—were crossbred successfully to homozygosity with Ig locus KO rats. This produced a highly efficient new multi-feature line (OmniRats™) with human $V_H$-D-$J_H$ regions of over 400 kb containing 22 functional $V_H$s and a rat C region of ~116 kb. DNA rearrangement, expression levels, class-switching and hypermutation was very similar between the different founders and comparable to wt rats. This is probably the result of the associated rat constant region accommodating several Cs and with the 3'E (enhancer control) region in authentic configuration.

B-Cell Development in the Knock-Out Background

To assess whether the introduced human Ig loci were capable of reconstituting normal B-cell development flow cytometric analyses were performed. Particular differentiation stages were analyzed in spleen and bone marrow lymphocytes (FIG. 2), which previously showed a lack of B-cell development in JKO/JKO rats[12], and no corresponding IgL expression in κKO/κKO as well as in λKO/λKO animals (data not shown). Most striking was the complete recovery of B-cell development in OmniRats compared to wt animals, with similar numbers of B220(CD45R)+ lymphocytes in bone marrow and spleen. IgM expression in a large proportion of CD45R+ B-cells marked a fully reconstituted immune system. Size and shape separation of spleen cells was indistinguishable between OmniRats and wt animals and thus successfully restored in the transgenic rats expressing human idiotypes with rat C region. Moreover, the small sIgG+ lymphocyte population was present in OmniRats (FIG. 2 right).

The analysis of other OmniRat lymphocyte tissues showed that they were indistinguishable from wt controls and, for example, T-cell subsets were fully retained (data not shown), which further supports the notion that optimal immune function has been completely restored.

Diverse Human H- and L-Chain Transcripts

Extensive transcriptional analysis was carried out using blood lymphocytes or spleen cells from transgenic rats with functional endogenous Ig loci. RT-PCR from specific human $V_H$ group forward to Cμ or Cγ reverse primers, showed human $V_H DJ_H$ usage. For L-chain analysis group specific human Vκ or Vλ forward primers were used with Cκ or Cλ reverse primers. The results (Table 3) showed the use of all integrated human $V_H$ genes regarded as functional[27] in combination with diverse use of D segments and all $J_H$ segments.

Figure 3:
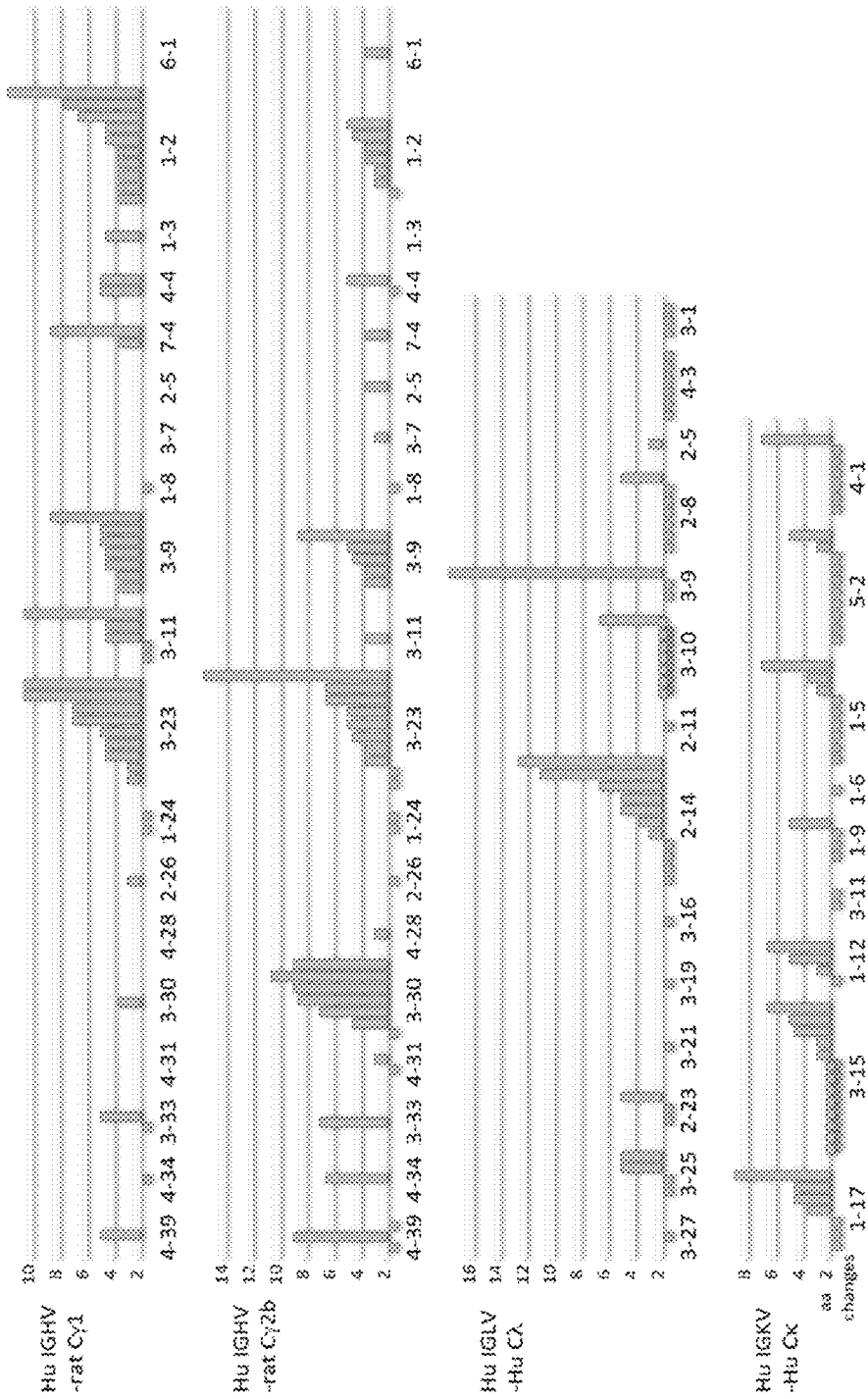
FIG. 3: Mutational changes in IgH and IgL transcripts from PBLs. Unique (VHDJH)s and VLs were from amplifications with V group specific primers: IGHV1, 2, 3, 4 and 6 in combination with the universal γCH2 reverse primer, IGLV2, 3 and 4 with reverse Cλ primer; and IGKV1, 3, 4 and 5 in with reverse Cκ primer (Supplementary Table 1). Mutated trans-switch products were identified for humanVH-rat Cγ2a (4) and human VH-rat Cγ2c (2).

The analysis of class-switch and hypermutation (FIG. 3) in the JKO/JKO background showed that these essential and highly desirable mechanisms are fully operative in OmniRats. Amplification of IgG switch products from PBLs revealed an extensive rate of mutation (>2 aa changes) in the majority of cells, ~80%, and in near equal numbers of γ1 and γ2b H-chains. A small percentage of trans-switch sequences, γ2a and 2c, were also identified (FIG. 3), which supports the observation that the translocus is similarly active, but providing human ($V_H$-D-$J_H$)s, as the endogenous IgH locus[28]. The number of mutated human Igγ and Igκ L-chain sequences is ~30% and thus considerably lower than IgG H-chains. The reason is the general amplification of L-chain from all producing cells rather than from IgG+ or differentiated plasma cells.

Ig Levels in Serum

To gain unambiguous information about antibody production we compared quality and quantity of serum Ig from OmniRats and normal wt animals. Purification of IgM and IgG separated on SDS-PAGE under reducing conditions (FIG. 4) showed the expected size—~75 kDa for μ, ~55 kDa for γ H-chains, and ~25 kDa for L-chains—which appeared indistinguishable between OmniRats and wt animals. The Ig yield from serum was determined to be between 100-300 μg/ml for IgM and 1-3 mg/ml for IgG for both, several OmniRats and wt animals. However, as rat IgG purification on protein A or G is seen as suboptimal[29], rat Ig levels may

TABLE 3

| | 4-39 | 3-38 | 3-35 | 4-34 | 3-33 | 4-31 | 3-30 | 4-28 | 2-26 | 1-24 | 3-23 | 3-22 | 3-11 | 3-9 | 1-8 | 3-7 | 2-5 | 7-4 | 4-4 | 1-3 | 1-2 | 6-1 |
|---|---|---|---|---|---|---|---|---|---|---|---|---|---|---|---|---|---|---|---|---|---|---|
| | IgH V | | | | | | | | | | | | | | | | | | | | | |
| HC14 | ✓ | | ✓ | ✓ | ✓ | ✓ | ✓ | ✓ | ✓ | ✓ | | ✓ | | ✓ | ✓ | ✓ | ✓ | ✓ | ✓ | ✓ | ✓ | ✓ |
| HC14 JKO/JKO | ✓ | | ✓ | ✓ | ✓ | ✓ | ✓ | ✓ | ✓ | ✓ | | ✓ | | ✓ | ✓ | ✓ | ✓ | ✓ | ✓ | ✓ | ✓ | ✓ |

| | 1-1 | 2-2 | 3-3 | 4-4 | 5-5 | 6-6 | 1-7 | 2-8 | 3-9 | 3-10 | 4-11 | 5-12 | 6-13 | 1-14 | 2-15 | 3-16 | 4-17 |
|---|---|---|---|---|---|---|---|---|---|---|---|---|---|---|---|---|---|
| | IgH D | | | | | | | | | | | | | | | | |
| HC14 | ✓ | ✓ | ✓ | | ✓ | ✓ | ✓ | | ✓ | ✓ | | ✓ | ✓ | | ✓ | ✓ | ✓ |
| HC14 JKO/JKO | | ✓ | | | ✓ | ✓ | ✓ | | ✓ | ✓ | | ✓ | ✓ | ✓ | ✓ | ✓ | ✓ |

| | 5-18 | 6-19 | 1-20 | 2-21 | 3-22 | 4-23 | 5-24 | 6-25 | 1-26 | 7-27 | 1 | 2 | 3 | 4 | 5 | 6 |
|---|---|---|---|---|---|---|---|---|---|---|---|---|---|---|---|---|
| | IgH D | | | | | | | | | | IgH J | | | | | |
| HC14 | ✓ | ✓ | ✓ | ✓ | ✓ | ✓ | ✓ | | ✓ | ✓ | | ✓ | ✓ | ✓ | ✓ | ✓ |
| HC14 JKO/JKO | ✓ | ✓ | | ✓ | ✓ | ✓ | ✓ | ✓ | ✓ | ✓ | ✓ | ✓ | ✓ | ✓ | ✓ | ✓ |

| | 3-27 | 3-25 | 2-23 | 3-22 | 3-21 | 3-19 | 2-18 | 3-16 | 2-14 | 3-12 | 2-11 | 3-10 | 3-9 | 2-8 | 4-3 | 3-1 | 1 | 2 | 3 |
|---|---|---|---|---|---|---|---|---|---|---|---|---|---|---|---|---|---|---|---|
| | IgL V | | | | | | | | | | | | | | | | IgL J | | |
| Hu L #6.2 | ✓ | ✓ | ✓ | | ✓ | ✓ | | ✓ | | ✓ | ✓ | ✓ | ✓ | ✓ | ✓* | ✓ | ✓ | ✓ | ✓ |

| | 1-17 | 1-16 | 3-15 | 1-12 | 3-11 | 1-9 | 1-8 | 3-7 | 1-6 | 1-5 | 5-2 | 4-1 | 1 | 2 | 3 | 4 | 5 |
|---|---|---|---|---|---|---|---|---|---|---|---|---|---|---|---|---|---|
| | IgK V | | | | | | | | | | | | IgK J | | | | |
| Hu K #79 | ✓ | ✓ | ✓ | ✓ | ✓ | ✓ | ✓ | ✓ | ✓ | ✓ | ✓ | ✓ | ✓ | ✓ | ✓ | ✓ | ✓ | be under represented. Taken into consideration that these young (~3 months old) rats were housed in pathogen-free facilities and had not been immunized, this compares well with the IgM levels of 0.5-1 mg/ml and IgG levels of several mgs/ml reported for rats kept in open facilities[30, 31]. Interestingly, we were able to visualize class-specific mobility of rat IgG isotypes on SDS-PAGE as demonstrated for monoclonals[29]. In IgG separations (FIG. 4b) a distinct lower γH-chain band is visible in wt but not OmniRat Ig. This band has been attributed to γ2a H-chains, which are not present in the OmniRat (HC14) translocus. As the IgG levels are similar between OmniRats and wt animals we assume class-switching is similarly efficient. The reason that the lack of Cγ2a in OmniRats is not limiting may be that several copies of the transgenic locus favorably increase the level of switch products. Purification of human Igκ and Igλ by capturing with anti-L-chain was also successful (FIGS. 4c and d) and predicted H- and L-chain bands were of the expected size. Confirmation of the IgM/G titers was also obtained by ELISA, which determined wt and OmniRat isotype distribution and identified comparable amounts of IgG1 and IgG2b (not shown).

A direct comparison of human Ig L-chain titers in solid phase titrations (FIGS. 4e and f) revealed 5-10 fold lower levels in OmniRats than in human serum. However, this was expected as human control serum from mature adults can sometimes contain over 10-times higher Ig levels than in children up to their teens[32], which would be similar to the human Igκ and Igλ titers in young rats. Interestingly, wt rats produce very little endogenous Igλ while transgenic rats can efficiently express both types of human L-chain, Igκ and Igλ.

Fully Human Antigen-Specific IgG

Several cell fusions were carried out, using either a rapid one-immunization scheme and harvesting lymph nodes or, alternatively, using booster immunizations and spleen cells (Table 2). For example, a considerable number of stable hybridomas were obtained after one immunization with human progranulin (PG) and myeloma fusion 22 days later. Here cell growth was observed in ~3,520 and ~1,600 wells in SD control and OmniRat hybridoma clones, respectively. Anti-progranulin specific IgG, characterized by biosensor measurements, was produced by 148 OmniRat clones. Limiting dilution, to exclude mixed wells, and repeat affinity measurements revealed that OmniRat clones retain their antigen specificity. A comparison of association and dissociation rates of antibodies from SD and OmniRat clones showed similar affinities between 0.3 and 74 nM (Table 4 and data not shown). Single immunizations with human growth hormone receptor (hGHR), TAU receptor coupled to keyhole limpet hemocyanin (TAU/KLH), hen egg lysozyme (HEL) or ovalbumin (OVA), followed by lymph node fusions also produced many high affinity human antibodies often at similar numbers compared to wt.

Furthermore, conventional booster immunizations with human PG, hGHR, human CD14 and HEL resulted in high affinities (pM range) of IgG with human idiotypes. OmniRats always showed the expected 4- to 5-log titer increase of antigen-specific serum IgG, similar to and as pronounced as wt rats (Table 4a). Although the results could vary from animal to animal, comparable numbers of hybridomas producing antigen-specific antibodies with similarly high affinities were obtained from wt animals (SD and other strains) and OmniRats. A summary of individual IgG producing lymph node and spleen cell fusion clones, showing their diverse human $V_H$-D-$J_H$, human Vκ-Jλ or Vλ-Jγ characteristics and affinities are presented in Table 4b. The immunization and fusion results showed that affinities well below 1 nM (determined by biosensor analysis) were frequently obtained from OmniRats immunized with PG, CD14, Tau, HEL and OVA antigens. In summary, antigen-specific hybridomas from OmniRats could be as easily generated as from wt animals yielding numerous mAbs with sub-nanomolar affinity even after a single immunization.

TABLE 4a

Diverse antigen-specific rat IgG hybridomas with fully human idiotypes[a]

| Animal | Antigen | Cells* | fusions | titer | hybrids | IgGs** | Kd*** |
|---|---|---|---|---|---|---|---|
| SD | PG | LN | 1 | 38400 | 3520 | 38 | 0.3-1.0 nM |
| OmniRat | PG | LN | 1 | 12800 | 1600 | 148 | 0.7-2.4 nM |
| SD | PG | SP | 1 | 51200 | 8000 | 29 | ND |
| OmniRat | PG | SP | 1 | 51200 | 36000 | 24 | ND |
| OmniRat | hGHR | LN | 3 | 4800 | 704-1024 | 18, 3, 2 | ND |
| SD | hGHR | SP | 1 | 204800 | 53760 | 230 | 0.07-0.4 nM |
| OmniRat | hGHR | SP | 1 | 76800 | 53760 | 7 | 0.16-2.4 nM |
| OmniRat | CD14 | SP | 2 | 102400 | 2800-3500 | 54, 14 | <0.1-0.2 nM |
| SD | TAU/KLH | LN | 1 | 20000 | 1728 | 99# | 0.6-2.4 nM |
| OmniRat | TAU/KLH | LN | 1 | 4800 | 1880 | 118# | 0.5-3.2 nM |
| SD | HEL | LN | 1 | 12800 | 1564 | 26 | 0.02-0.1 nM |
| OmniRat | HEL | LN | 3 | 25600 | 288-640 | 0, 2, 7 | 0.6-1.5 nM |
| SD | HEL | SP | 1 | 6400 | 30720 | 0 | ND |
| SD | OVA | LN | 1 | 9600 | 1488 | 10 | 1.1-4.8 nM |
| OmniRat | OVA | LN | 4 | 8000 | 512-2240 | 0, 30, 0, 1 | 0.7-1.5 nM |

*cell numbers were 3-9 × 10^7 per fusion
**antigen specificity confirmed by biosensor analysis
***range of 5 highest affinities
8 mAbs were specific for Tau-peptide TABLE 4b

| Antigen | Fusion Cells[a] | Clone | $K_D$ (nM) | IGHV | AA changes | IGHD |
|---|---|---|---|---|---|---|
| PG | LN | 8080.1B2 | 0.7 | 4-31 | 2 | 7-27 |
| PG | LN | 8080.2B3 | 1.4 | 3-23 | 1 | 3-3 |

TABLE 4b-continued

| Antigen | Fusion Cells[a] | Clone | $K_D$ (nM) | IGHV | AA changes | IGHD |
|---|---|---|---|---|---|---|
| hGHR | LN | 9045.8A3 | 2.4 | 1-2 | 6 | 6-19 |
| hGHR | LN | 9046.6E10 | 4.2 | 1-2 | 7 | 3-16 |
| TAU/KLH | LN | 8898.2B10 | 0.8 | 4-39 | 5 | 3-22 |
| OVA | LN | 9477.2F4 | 2.7 | 3-23 | 6 | 1-26 |
| OVA | LN | 9477.2A9 | 3.9 | 3-11 | 5 | 3-10 |
| HEL | SP | 1H2 | 0.9 | 3-23 | 15 | 6-19 |
| HEL | SP | 3C10 | 0.8 | 6-1 | 1 | 6-19 |
| β-gal | SP | 5005.6C1 | nd | 6-1 | 5 | 2-21 |

| Antigen | IGHJ | CDR3 | IGκ/λV | AA changes | IGκ/λJ |
|---|---|---|---|---|---|
| PG | 3 | CATGTGEDAFDIW | LV3-10 | 1 | 2 or 3 |
| PG | 4 | CAKGIGSALITPPDYW | LV3-19 | 2 | 2 or 3 |
| hGHR | 3 | CARVGQWLNAFDIW | LV2-14 | 9 | 2 or 3 |
| hGHR | 4 | CARRGDGAFDYW | LV2-23 | 5 | 2 or 3 |
| TAU/KLH | 4 | CARHRYYYDSRGYFIFDYW | KV4-1 | 0 | 2 |
| OVA | 4 | CAKEWGYGGSYPFDYW | KV1-17 | 1 | 5 |
| OVA | 4 | CARAYYYGSGSSLFDYW | KV1-6 | 12 | 4 |
| HEL | 4 | CAKREYSSDWYPFDHW | KV3-11 | 1 | 2 |
| HEL | 1 | CAREGSSGWYGFFQHW | KV1-5 | 0 | 5 |
| β-gal | 4 | CARTPRLGLPFDYW | KV1-12 | 0 | 4 |

[a]OmniRats (HC14/Huκ and/or Huλ/JKOJKO/KKOKKO) and control SD rats were immunized with human prograulm (PG), human growth hormone receptor (hGHR), human CD14, Tau-peptide (TAU-KLH), hen egg lysozyme (HEL), ovalbumin (OVA) or β-galactosidase (β-gal).
*Lymph nodes (LN) or spleen cells (SP) were fused after single or multiple administration of antigen, respectively.

Discussion

A combination of human and rat genes to assemble a novel IgH locus has resulted in highly efficient near normal expression of antibodies with human idiotypes. Moreover, integration of the human Igκ and Igλ loci revealed that chimeric Ig with fully human specificity is readily produced and that association of rat C-regions with human L-chains is not detrimental. Advantages of using part of the rat IgH locus are that species-specific C regions and enhancer control elements are kept in their natural configuration, with essentially only the diverse human $V_H$ D $J_H$ region being transplanted. Furthermore, expression of antibodies with rat Fc-regions allow normal B-cell receptor assembly and optimal activation of the downstream signaling pathway essential for the initiation of highly efficient immune responses. In particular, the quality of an immune response to antigen challenge relies on combined actions of many receptor associated signaling and modifier components (see: www.biocarta.com/pathfiles/h_bcrpathway.asp).

The approach of using YACs and BACs, and interchanging between the two, has the advantage of both, speed and the ability to check integrity when making constructs of large regions by overlapping homology. Several founder rats carried low translocus copy numbers; with the rat C-gene BAC in OmniRat likely to be fully integrated in 5 copies as determined by qPCR of Cμ and Cα products (not shown). Identification by FISH of single position insertion in many lines (see Table 1d) confirmed that spreading or multiple integration of BAC mixtures were rare; an advantage for breeding to homozygosity, which was achieved. Little was known whether extensive overlapping regions would integrate, such as to maintain the full functionality, essential for DNA rearrangement. Previously, overlapping integration has been reported but for much smaller regions (<100 kb)[24, 33] and our results suggest that desired integration by homology or in tandem is a frequent event. This eases the transgenic technology substantially as no laborious integration of large YACs into stem cells and subsequent animal derivation therefrom has to be performed[18, 19]. In addition, ZFN technology, also performed via DNA injection[11, 12], produced Ig KO strains easily and may well be the future technology of choice for gene disruptions and replacement. Silenced endogenous Ig gene expression in OmniRats, containing human-rat IgH and human IgL loci, has the advantage that no interfering or undesired rat Ig could give rise to mixed products. Interestingly, immunization and hybridoma generation in OmniRats still producing wt Ig revealed that many products were fully human, human-rat IgH and human IgL, despite incomplete Ig KOs. Here, despite the extensive number of wt V genes, it was remarkable that the introduced human genes amplified readily and thus showed to be efficient expression competitors. This is in line with the observation of generally good expression levels of all our integrated transgenes, which favorably compete with the endogenous loci. Previously in mice expressing a human antibody repertoire, Ig KOs were essential as little expression of human products was found when wt Ig is released[8, 18].

It is possible that the production of fully human Ig loci even in Ig KO mice is suboptimal as strain specific cis-acting sequences are required for high-level expression. In the mouse an enhancer region downstream of Cα plays a vital role in class-switch recombination[34] and it is likely that elements in that region may facilitate hypermutation[23]. This may be the reason why immune responses and generation of diverse hybridomas at high frequency may be difficult in mice carrying even a large fully human locus[35, 36]. As the chimeric human-rat IgH locus facilitates near wt differentiation and expression levels in OmniRats, it can be concluded that the endogenous rat C region and indeed the ~30 kb enhancer sequence 3' of Cα are providing optimal locus control to express and mature human $V_H$ genes. Another region, Cδ with its 3' control motif cluster[26], has been removed from the chimeric C-region BAC since silencing or a lack of IgD did not appear to reduce immune function[37 and refs therein]. Normally, mature IgM$^+$IgD$^+$ B-cells down-regulate IgD upon antigen contact, which initiates class-switch recombination[37]. Thus, switching may be increased without IgD control, which is supported by our finding that IgG transcripts and serum levels are significantly lower when the Cδ region is retained in transgenic constructs (data not shown).

The production of specific IgG in OmniRats is particularly encouraging as we found that in various immunizations mAbs with diversity in sequence and epitope, comparable to what was produced in wt controls, could be isolated via spleen and lymph node fusion. V-gene, D and J diversity was as expected and nearly all segments were found to be used productively as predicted[27]. This was in stark contrast to mice carrying fully human transloci where clonal expansion from a few precursor B-cells produced little diversity[23]. Since the number of transplanted V-genes is only about half of what is used in humans we anticipated to find restricted immune responses and limited diversity when comparing OmniRats with wt animals. However, this was not the case and a comparison of CDR3 diversity in over 1000 clones (sequences can be provided) revealed the same extensive junctional differences in OmniRats as in wt animals. The few identical gene-segment combinations were further diversified by N-sequence additions or deletion at the $V_H$ to D and/or D to $J_H$ junctions and also by hypermutation. Thus, it is clear that the rat C region sequence is highly efficient in controlling DNA rearrangement and expression of human $V_H DJ_H$. Extensive diversity was also seen for the introduced human Igκ and Igλ loci, similar to what has previously been shown in mice[22, 23, 38]. Hence, substantially reduced efficiency in the production of human antibodies from mice[7] has been overcome in OmniRats, which diversify rearranged H-chains reliably and extensively by class-switch and hypermutation to yield high affinity antibodies in bulk rather than occasionally. The yield of transgenic IgG and the level of hypermutation, impressively utilized in antigen-specific mAbs, showed that clonal diversification and production level are similar between OmniRats and wt animals. Routine generation of high affinity specificities in the subnanomolar range was even accomplished by different single immunizations and again compares favorably with wt animals; results that have not been shown in transgenic mice producing human antibody repertoires from entirely human loci[18].

In summary, to maximize human antibody production an IgH locus that uses human genes for antibody specificity but rodent genes for control of differentiation and high expression should be regarded essential. L-chain flexibility is a bonus as it permits highly efficient human IgH/IgL assembly even when wt Ig is present. For therapeutic applications chimeric H-chains can be easily converted into fully human Abs by C-gene replacement without compromising the specificity.

All patents and patent publications referred to herein are hereby incorporated by reference.

Certain modifications and improvements will occur to those skilled in the art upon a reading of the foregoing description. It should be understood that all such modifications and improvements have been deleted herein for the sake of conciseness and readability but are properly within the scope of the following claims.

REFERENCES

1. Chan, A. C. & Carter, P. J. Therapeutic antibodies for autoimmunity and inflammation. *Nature reviews. Immunology* 10, 301-316 (2010).
2. Enever, C., Batuwangala, T., Plummer, C. & Sepp, A. Next generation immunotherapeutics—honing the magic bullet. *Current opinion in biotechnology* 20, 405-411 (2009).
3. Brüggemann, M., Smith, J. A., Osborn, M. J. & Zou, X. Part I: Selecting and shaping the antibody molecule, Selection Strategies III: Transgenic mice, in Handbook of Therapeutic Antibodies. Ed. Dübel, S. *Wiley-VHC*, 69-93 (2007).
4. Green, L. L. Antibody engineering via genetic engineering of the mouse: XenoMouse strains are a vehicle for the facile generation of therapeutic human monoclonal antibodies. *Journal of immunological methods* 231, 11-23 (1999).
5. Ishida, I. et al. Production of human monoclonal and polyclonal antibodies in TransChromo animals. *Cloning and stem cells* 4, 91-102 (2002).
6. Kuroiwa, Y. et al. Cloned transchromosomic calves producing human immunoglobulin. *Nature biotechnology* 20, 889-894 (2002).
7. Lonberg, N. Human antibodies from transgenic animals. *Nature biotechnology* 23, 1117-1125 (2005).
8. Bruggemann, M. et al. A repertoire of monoclonal antibodies with human heavy chains from transgenic mice. *Proceedings of the National Academy of Sciences of the United States of America* 86, 6709-6713 (1989).
9. Kitamura, D., Roes, J., Kuhn, R. & Rajewsky, K. A B cell-deficient mouse by targeted disruption of the membrane exon of the immunoglobulin mu chain gene. *Nature* 350, 423-426 (1991).
10. Davies, N. P. & Bruggemann, M. Extension of yeast artificial chromosomes by cosmid multimers. *Nucleic acids research* 21, 767-768 (1993).
11. Geurts, A. M. et al. Knockout rats via embryo microinjection of zinc-finger nucleases. *Science* 325, 433 (2009).
12. Menoret, S. et al. Characterization of immunoglobulin heavy chain knockout rats. *European journal of immunology* 40, 2932-2941 (2010).
13. Flisikowska, T. et al. Efficient immunoglobulin gene disruption and targeted replacement in rabbit using zinc finger nucleases. *PloS one* 6, e21045 (2011).
14. Xian, J. et al. Comparison of the performance of a plasmid-based human Igκ minilocus and YAC-based human Igκ transloci for the production of a human antibody repertoire in transgenic mice. *Transgenics*, 333-343 (1998).
15. Anand, R. Yeast artificial chromosomes (YACs) and the analysis of complex genomes. *Trends Biotechnol* 10, 35-40 (1992).
16. Davies, N. P., Rosewell, I. R. & Bruggemann, M. Targeted alterations in yeast artificial chromosomes for inter-species gene transfer. *Nucleic acids research* 20, 2693-2698 (1992).
17. Zou, X., Xian, J., Davies, N. P., Popov, A. V. & Bruggemann, M. Dominant expression of a 1.3 Mb human Ig kappa locus replacing mouse light chain production. *FASEB journal: official publication of the Federation of American Societies for Experimental Biology* 10, 1227-1232 (1996).

18. Mendez, M. J. et al. Functional transplant of megabase human immunoglobulin loci recapitulates human antibody response in mice. *Nature genetics* 15, 146-156 (1997).

19. Davies, N. P. et al. Creation of mice expressing human antibody light chains by introduction of a yeast artificial chromosome containing the core region of the human immunoglobulin kappa locus. *Biotechnology* (N Y) 11, 911-914 (1993).

20. Davies, N. P., Popov, A. V., Zou, X. & Brüggemann, M. Human antibody repertoires in transgenic mice: Manipulation and transfer of YACs. *IRL Oxford*, 59-76 (1996).

21. Lonberg, N. et al. Antigen-specific human antibodies from mice comprising four distinct genetic modifications. *Nature* 368, 856-859 (1994).

22. Nicholson, I. C. et al. Antibody repertoires of four- and five-feature translocus mice carrying human immunoglobulin heavy chain and kappa and lambda light chain yeast artificial chromosomes. *J Immunol* 163, 6898-6906 (1999).

23. Pruzina, S. et al. Human monoclonal antibodies to HIV-1 gp140 from mice bearing YAC-based human immunoglobulin transloci. *Protein engineering, design & selection: PEDS* 24, 791-799 (2011).

24. Wagner, S. D., Gross, G., Cook, G. P., Davies, S. L. & Neuberger, M. S. Antibody expression from the core region of the human IgH locus reconstructed in transgenic mice using bacteriophage P1 clones. *Genomics* 35, 405-414 (1996).

25. Popov, A. V., Butzler, C., Frippiat, J. P., Lefranc, M. P. & Bruggemann, M. Assembly and extension of yeast artificial chromosomes to build up a large locus. *Gene* 177, 195-201 (1996).

26. Mundt, C. A. et al. Novel control motif cluster in the IgH delta-gamma 3 interval exhibits B cell-specific enhancer function in early development. *J Immunol* 166, 3315-3323 (2001).

27. Lefranc, M.-P. & Lefranc, G. The immunoglobulin factsbook. *FactsBook Series, Academic Press, GB*, 45-68 (2001).

28. Reynaud, S. et al. Interallelic class switch recombination contributes significantly to class switching in mouse B cells. *J Immunol* 174, 6176-6183 (2005).

29. Bruggemann, M., Teale, C., Clark, M., Bindon, C. & Waldmann, H. A matched set of rat/mouse chimeric antibodies. Identification and biological properties of rat H chain constant regions mu, gamma 1, gamma 2a, gamma 2b, gamma 2c, epsilon, and alpha. *J Immunol* 142, 3145-3150 (1989).

30. Bazin, H., Beckers, A. & Querinjean, P. Three classes and four (sub)classes of rat immunoglobulins: IgM, IgA, IgE and IgG1, IgG2a, IgG2b, IgG2c. *European journal of immunology* 4, 44-48 (1974).

31. McGhee, J. R., Michalek, S. M. & Ghanta, V. K. Rat immunoglobulins in serum and secretions: purification of rat IgM, IgA and IgG and their quantitation in serum, colostrum, milk and saliva. *Immunochemistry* 12, 817-823 (1975).

32. Shansab, M., Eccleston, J. M. & Selsing, E. Translocation of an antibody transgene requires AID and occurs by interchromosomal switching to all switch regions except the mu switch region. *European journal of immunology* 41, 1456-1464 (2011).

33. Bruggemann, M. et al. Human antibody production in transgenic mice: expression from 100 kb of the human IgH locus. *European journal of immunology* 21, 1323-1326 (1991).

34. Vincent-Fabert, C. et al. Genomic deletion of the whole IgH 3' regulatory region (hs3a, hs1,2, hs3b, and hs4) dramatically affects class switch recombination and Ig secretion to all isotypes. *Blood* 116, 1895-1898 (2010).

35. Davis, C. G., Gallo, M. L. & Corvalan, J. R. Transgenic mice as a source of fully human antibodies for the treatment of cancer. *Cancer metastasis reviews* 18, 421-425 (1999).

36. Lonberg, N. Fully human antibodies from transgenic mouse and phage display platforms. *Current opinion in immunology* 20, 450-459 (2008).

37. Chen, K. C., A. New Insights into the Enigma of Immunoglobulin D. *Immunol Rev* 237, 160-179 (2010).

38. Popov, A. V., Zou, X., Xian, J., Nicholson, I. C. & Bruggemann, M. A human immunoglobulin lambda locus is similarly well expressed in mice and humans. *The Journal of experimental medicine* 189, 1611-1620 (1999).

39. Marchuk, D. & Collins, F. S. pYAC-R C, a yeast artificial chromosome vector for cloning DNA cut with infrequently cutting restriction endonucleases. *Nucleic acids research* 16, 7743 (1988).

40. Kaur, R., Ma, B. & Cormack, B. P. A family of glycosylphosphatidylinositol-linked aspartyl proteases is required for virulence of Candida glabrata. *Proceedings of the National Academy of Sciences of the United States of America* 104, 7628-7633 (2007).

41. Nelson, D. L. & Brownstein, B. H. YAC libraries: A user's guide. *Freeman and Company, NY* (1994).

42. Gietz, D. & Woods, R. A. Transformation of yeast by the lithium acetate single-stranded carrier DNA/PEG method. *Methods in Microbiology* 26, 53-66 (1998).

43. Peterson, K. R. Preparation of intact yeast artificial chromosome DNA for transgenesis of mice. *Nature protocols* 2, 3009-3015 (2007).

44. Beverly, S. M. Characterization of the 'unusual' mobility of large circular DNAs in pulsed field-gradient electrophoresis *Nucleic acids research* 16, 925-939 (1988).

45. Kawasaki, K. et al. Evolutionary dynamics of the human immunoglobulin kappa locus and the germline repertoire of the Vkappa genes. *European journal of immunology* 31, 1017-1028 (2001).

46. Sambrook, J. & Russell, D. W. Molecular Cloning. A laboratory Manual. *Cold Spring Harbor Laboratory Press, NY* (2001).

47. Gu, H., Wilson, D. & Inselburg, J. Recovery of DNA from agarose gels using a modified Elutrap. *Journal of biochemical and biophysical methods* 24, 45-50 (1992).

48. Yang, X. W., Model, P. & Heintz, N. Homologous recombination based modification in *Escherichia coli* and germline transmission in transgenic mice of a bacterial artificial chromosome. *Nature biotechnology* 15, 859-865 (1997).

49. Meisner, L. M., and J. Johnson Protocols for cytogenetic studies of human embryonic stem cells. *Methods* 45, 133-141 (2008).

50. Kishiro, Y., Kagawa, M., Naito, I. & Sado, Y. A novel method of preparing rat-monoclonal antibody-producing hybridomas by using rat medial iliac lymph node cells. *Cell structure and function* 20, 151-156 (1995).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09475859B2). An electronic copy of the "Sequence Listing" will also be available from the USPTO upon request and payment of the fee set forth in 37 CFR 1.19(b)(3).

The invention claimed is:

1. A transgenic rodent, the rodent comprising in its germline a heavy chain immunoglobulin locus comprising human unrearranged heavy chain variable region gene segments linked to DNA encoding a rodent heavy chain constant region and a rat 3' enhancer comprising the sequence set forth as SEQ ID NO:1, wherein the heavy chain immunoglobulin locus does not comprise a human immunoglobulin constant region gene, and wherein the rodent is a mouse or a rat.

2. The rodent of claim 1, wherein the human heavy chain variable region gene segments are contained on a DNA fragment that is larger than 170 kb.

3. The rodent of claim 1, wherein the human heavy chain variable region gene segments are contained on a DNA fragment that is larger than 180 kb.

4. The rodent of claim 1, wherein the human heavy chain variable region gene segments are contained on a DNA fragment that is larger than 350 kb.

5. The rodent of claim 1, wherein the human unrearranged heavy chain variable region gene segments are capable of rearranging to form a functional heavy chain variable region gene.

6. The rodent of claim 5, wherein following rearrangement the rodent expresses a functional antigen-binding molecule encoded by the human gene segments.

7. The rodent of claim 1, wherein the rodent produces an antibody that comprises a human variable region and a rodent constant region.

8. The rodent of claim 1, wherein the rodent is a rat.

9. The rodent of claim 1, wherein the rodent heavy chain constant region is a rodent Fc region.

10. A method of producing an antibody having a human variable region and a rodent constant region comprising exposing a transgenic rodent to an antigen, the rodent comprising in its germline a heavy chain immunoglobulin locus comprising human unrearranged heavy chain variable region gene segments linked to DNA encoding a rodent heavy chain constant region and a rat 3' enhancer comprising the sequence set forth as SEQ ID NO:1, wherein the heavy chain immunoglobulin locus does not comprise a human immunoglobulin constant region gene, wherein the exposure to the antigen is such that the transgenic rodent produces an antibody to the antigen, the antibody having a human heavy chain variable region and a rodent heavy chain constant region, and wherein the rodent is a mouse or a rat.

11. The method of claim 10, wherein the human heavy chain variable region gene segments are contained on a DNA fragment that is larger than 170 kb.

12. The method of claim 10, wherein the human heavy chain variable region gene segments are contained on a DNA fragment that is larger than 180 kb.

13. The method of claim 10, wherein the human heavy chain variable region gene segments are contained on a DNA fragment that is larger than 350 kb.

14. The method of claim 10, wherein the rodent is a rat.

15. The method of claim 10, wherein the rodent heavy chain constant region is a rodent Fc region.

16. The method of claim 10, further comprising the step of making a hybridoma from the transgenic rodent, the hybridoma comprising DNA encoding the antibody.

17. The method of claim 16, wherein the hybridoma is made from the spleen of the transgenic rodent.

* * * * *